(12) United States Patent
Solomon

(10) Patent No.: US 12,290,811 B2
(45) Date of Patent: May 6, 2025

(54) MICROFLUIDIC SERIAL DILUTION PLATFORM BASED WELL-PLATE USING AN OIL-FREE IMMISCIBLE PHASE DRIVEN BY MANUAL OR ELECTRONIC PIPETTORS

(71) Applicant: Unchained Labs, Pleasanton, CA (US)

(72) Inventor: Deepak Solomon, San Diego, CA (US)

(73) Assignee: Unchained Labs, Pleasanton, CA (US)

( * ) Notice: Subject to any disclaimer, the term of this patent is extended or adjusted under 35 U.S.C. 154(b) by 1075 days.

(21) Appl. No.: 17/134,737

(22) Filed: Dec. 28, 2020

(65) Prior Publication Data

US 2021/0114022 A1   Apr. 22, 2021

Related U.S. Application Data

(63) Continuation-in-part of application No. 15/005,341, filed on Jan. 25, 2016, now Pat. No. 10,875,017.
(Continued)

(51) Int. Cl.
*B01L 3/00*     (2006.01)
*G01N 33/543*   (2006.01)
*G01N 35/10*    (2006.01)

(52) U.S. Cl.
CPC ....... *B01L 3/50273* (2013.01); *B01L 2200/06* (2013.01); *B01L 2200/0647* (2013.01);
(Continued)

(58) Field of Classification Search
CPC ..... B01L 2300/0838; B01L 2300/0864; B01L 2300/0883; B01L 2400/0406;
(Continued)

(56) References Cited

U.S. PATENT DOCUMENTS 723,826 A    3/1903   Buysse
5,932,418 A  8/1999   Yager
(Continued)

FOREIGN PATENT DOCUMENTS

AU   2013204820 B2   1/2014
CA   2521862         10/2012
(Continued)

OTHER PUBLICATIONS

Final Rejection dated Dec. 12, 2019, from U.S. Appl. No. 15/005,341, 34 sheets.
(Continued)

*Primary Examiner* — Jennifer Wecker
*Assistant Examiner* — Bryan Kilpatrick
(74) *Attorney, Agent, or Firm* — COOLEY LLP

(57) ABSTRACT

Described is a microfluidic serial dilution platform based well-plate using an oil-free immiscible phase driven by manual or electronic pipettors. The well-plate includes a plurality of fluidic traps, a plurality of hydrophilic capillary constriction channels and a plurality of bypass channels. Each of the plurality of bypass channels is associated with one of the plurality of fluidic traps, each of the plurality of hydrophilic capillary constriction channels is associated with one of the plurality of fluidic traps, and each of the plurality of fluidic traps is associated with one of the plurality of bypass channels and one of the plurality of hydrophilic capillary constriction channels. The well-plate further includes an inlet, an outlet, and a main channel with a plurality of portions that connects the inlet to the plurality of fluidic traps, associated hydrophilic capillary constriction channels and associated bypass channels, and the outlet.

25 Claims, 24 Drawing Sheets

Related U.S. Application Data

(60) Provisional application No. 62/107,132, filed on Jan. 23, 2015.

(52) U.S. Cl.
CPC .............. *B01L 2300/0829* (2013.01); *B01L 2300/0867* (2013.01); *B01L 2300/087* (2013.01); *B01L 2300/0877* (2013.01); *B01L 2300/088* (2013.01); *B01L 2300/161* (2013.01); *G01N 33/54366* (2013.01); *G01N 35/10* (2013.01)

(58) Field of Classification Search
CPC .............. B01L 3/502715; G01N 1/38; G01N 2001/383; G01N 33/54366; G01N 35/10
See application file for complete search history.

(56) References Cited

U.S. PATENT DOCUMENTS

| | | | |
|---|---|---|---|
| 6,048,734 | A | 4/2000 | Burns et al. |
| 6,293,012 | B1 | 9/2001 | Moles |
| 6,319,469 | B1 | 11/2001 | Mian et al. |
| 7,708,949 | B2 | 5/2010 | Stone et al. |
| 8,592,221 | B2 | 11/2013 | Fraden et al. |
| 8,765,485 | B2 | 7/2014 | Link et al. |
| 9,315,768 | B2 | 4/2016 | Vrouwe et al. |
| 10,875,017 | B2 * | 12/2020 | Solomon .......... B01L 3/502715 |
| 10,981,166 | B2 | 4/2021 | Solomon |
| 11,305,279 | B2 | 4/2022 | Solomon |
| 2002/0033193 | A1 | 3/2002 | McNeely et al. |
| 2002/0036018 | A1 | 3/2002 | McNeely |
| 2002/0075363 | A1 | 6/2002 | McNeely et al. |
| 2002/0097633 | A1 | 7/2002 | O'Connor |
| 2003/0138829 | A1 | 7/2003 | Unger et al. |
| 2003/0159999 | A1 | 8/2003 | Oakey et al. |
| 2004/0072278 | A1 | 4/2004 | Chou et al. |
| 2004/0137607 | A1 | 7/2004 | Tanaami |
| 2004/0206408 | A1 | 10/2004 | Peters et al. |
| 2006/0018790 | A1 | 1/2006 | Naka et al. |
| 2007/0037199 | A1 | 2/2007 | Takahashi et al. |
| 2007/0110631 | A1 | 5/2007 | Ajdari |
| 2007/0125942 | A1 | 6/2007 | Kido |
| 2007/0195127 | A1 | 8/2007 | Ahn et al. |
| 2008/0233607 | A1 | 9/2008 | Yu et al. |
| 2009/0136982 | A1 | 5/2009 | Tang et al. |
| 2009/0151792 | A1 | 6/2009 | Noda |
| 2010/0165784 | A1 | 7/2010 | Jovanovich et al. |
| 2010/0221831 | A1 | 9/2010 | Miyazaki et al. |
| 2010/0252118 | A1 | 10/2010 | Fraden |
| 2011/0256574 | A1 | 10/2011 | Zhang et al. |
| 2011/0269226 | A1 | 11/2011 | Van Noort et al. |
| 2011/0301058 | A1 | 12/2011 | Cheng et al. |
| 2012/0219947 | A1 | 8/2012 | Yurkovetsky |
| 2012/0244043 | A1 | 9/2012 | Leblanc |
| 2013/0136694 | A1 | 5/2013 | Russo Da Conceição Martinho et al. |
| 2013/0236376 | A1 | 9/2013 | Augstein et al. |
| 2013/0280131 | A1 | 10/2013 | Handique et al. |
| 2013/0337578 | A1 | 12/2013 | Delamarche et al. |
| 2014/0051062 | A1 | 2/2014 | Vanapalli et al. |
| 2014/0246098 | A1 | 9/2014 | Fraden et al. |
| 2014/0302160 | A1 | 10/2014 | Achrol et al. |
| 2014/0377850 | A1 | 12/2014 | Handique et al. |
| 2015/0044688 | A1 | 2/2015 | Richter et al. |
| 2015/0125947 | A1 | 5/2015 | Korczyk et al. |
| 2015/0184127 | A1 | 7/2015 | White et al. |
| 2016/0214104 | A1 | 7/2016 | Schwemmer et al. |
| 2016/0332163 | A1 | 11/2016 | Wang et al. |
| 2016/0361715 | A1 | 12/2016 | Shi et al. |
| 2016/0361716 | A1 | 12/2016 | Solomon |
| 2017/0232440 | A1 | 8/2017 | Ismagilov et al. |
| 2018/0071735 | A1 | 3/2018 | Linder et al. |
| 2019/0054467 | A1 | 2/2019 | Handique |
| 2020/0055051 | A1 | 2/2020 | Solomon et al. |
| 2020/0179930 | A1 | 6/2020 | Solomon |
| 2020/0261910 | A1 | 8/2020 | Solomon |
| 2022/0266212 | A1 | 8/2022 | Solomon |

FOREIGN PATENT DOCUMENTS

| | | | |
|---|---|---|---|
| EP | | 2364774 A3 | 6/2016 |
| EP | | 3615220 A1 | 3/2020 |
| FR | | 2897282 A1 | 8/2007 |
| JP | | 2000515630 A | 11/2000 |
| JP | | 2004163104 A | 6/2004 |
| WO | WO-2006052223 A1 | | 5/2006 |
| WO | | 2006096571 A2 | 9/2006 |
| WO | WO-2008097559 A2 | | 8/2008 |
| WO | WO-2008130623 A1 | | 10/2008 |
| WO | | 2010111231 A1 | 9/2010 |
| WO | | 2012154688 A2 | 11/2012 |
| WO | WO-2016118949 A1 | | 7/2016 |
| WO | | 2016/187561 A1 | 11/2016 |
| WO | | 2016/201430 A1 | 12/2016 |
| WO | WO-2016201163 A1 | | 12/2016 |
| WO | WO-2017027838 A1 | | 2/2017 |
| WO | WO-2017180949 A1 | | 10/2017 |
| WO | WO-2018200896 A1 | | 11/2018 |
| WO | WO-2019032690 A1 | | 2/2019 |
| WO | WO-2019094775 A1 | | 5/2019 |
| WO | WO-2020087032 A2 | | 4/2020 |
| WO | WO-2021067353 A1 | | 4/2021 |
| WO | WO-2022146770 A1 | | 7/2022 |
| WO | WO-2023023492 A1 | | 2/2023 |

OTHER PUBLICATIONS

Non-Final Rejection dated Jun. 3, 2019, from U.S. Appl. No. 15/005,341, 33 sheets.
Final Rejection dated Feb. 4, 2019, from U.S. Appl. No. 15/005,341, 42 sheets.
Non-Final Rejection dated Mar. 9, 2018, from U.S. Appl. No. 15/005,341, 15 sheets.
Notice of Allowanced dated Dec. 4, 2020, from U.S. Appl. No. 15/005,341, 7 sheets.
Notice of Allowanced dated Aug. 21, 2020, from U.S. Appl. No. 15/005,341, 36 sheets.
Resto, Pedro J. et al., "High Speed Droplet-based Delivery System for Passive Pumping in Microfluidic Devices", Sep. 2, 2009, Journal of Visual Experiments, Issue 31, p. 1-5. (Year: 2009).
Communication pursuant to Article 94(3) EPC for European Patent Application No. 16 740 896.2 with a mailing date of May 9, 2019.
International Search Report dated Jun. 2, 2016 for PCT/US16/14704.
Clausell-Tormos, et al., "An Automated Two-phase Microfluidic System for Kinetic Analyses and the Screening of Compound Libraries," Lab on a Chip, 2010, Issue 10, pp. 1302-1307.
Communication pursuant to Article 94(3) EPC for European Patent Application No. 18206472.5 with a mailing date of Jan. 7, 2020. 5 pages.
Communication pursuant to Article 94(3) EPC for European Patent Application No. 18206472.5 with a mailing date of Sep. 16, 2020, 5 pages.
Extended European Search Report for European Patent Application No. 16808519.9, with a mailing date of Nov. 12, 2018. 9 pages.
Extended European Search Report for European Patent Application No. 18206472.5, with a mailing date of Jan. 22, 2019. 9 pages.
Extended European Search Report mailed on Dec. 1, 2020, for EP Application No. 18791954.3, filed on Apr. 27, 2018, 7 pages.
Extended European Search Report mailed on Jul. 28, 2021, for EP Application No. 18 844 318.8, filed on Aug. 8, 2018, 12 pages.
Extended European Search Report mailed on Oct. 10, 2022, for EP Application No. 19876942.4, filed on Oct. 25, 2019, 9 pages.
Extended European Search Report mailed on Oct. 5, 2021 for EP Application No. 18876268.6, filed Nov. 9, 2018, 9 pages.
International Application No. PCT/US2018/060104, International Search Report dated Feb. 28, 2019, 14 pages.

(56) References Cited

OTHER PUBLICATIONS

International Search Report and Written Opinion for International Application No. PCT/US2022/074985 dated Jan. 6, 2023, 18 pages.
International Search Report mailed on Oct. 23, 2018, for PCT Application No. PCT/US2018/045793, filed on Aug. 8, 2018, 2 pages.
International Application No. PCT/US2018/029692, International Search Report mailed Jul. 12, 2018, 4 pages.
International Search Report and Written Opinion dated Sep. 1, 2016 for PCT Application No. PCT/US2016/037225 filed Jun. 13, 2016. 5 pages.
International Search Report and Written Opinion mailed on Jan. 15, 2020, for PCT Application No. PCT/US2019/058202, 8 pages.
International Search Report and Written Opinion mailed on Jun. 15, 2022, for PCT Application No. PCT/US2021/064512, filed on Dec. 21, 2021, 19 pages.
International Search Report and Written Opinion of the International Searching Authority mailed on Jul. 12, 2018, for PCT Application No. PCT/US2018/029692, 22 pages.
Notice of Allowance mailed on Jan. 18, 2023, for U.S. Appl. No. 16/637,406, filed Feb. 7, 2020, 12 pages.
Notice of Allowance mailed on Nov. 9, 2022, for U.S. Appl. No. 16/637,406, filed Feb. 7, 2020, 12 pages.
Notice of Allowance mailed on Apr. 5, 2023, for U.S. Appl. No. 17/722,246, filed Apr. 15, 2022, 11 pages.
Partial Supplementary European Search Report mailed on Apr. 21, 2021, for EP Application No. 18 844 318.8, filed on Aug. 8, 2018, 12 pages.
Written Opinion mailed on Jun. 2, 2016, for PCT Application No. PCT/US2016/014704, filed on Jan. 25, 2016, 8 pages.
Written Opinion of the International Searching Authority mailed on Oct. 23, 2018, for PCT Application No. PCT/US2018/045793, filed on Aug. 8, 2018, 10 pages.
Zhu and Wang, "Passive and active droplet generation with Microfluidics: a review" Lab Chip (2017) 17:34-75.
Communication pursuant to Article 94(3) EPC for European Patent Application No. 16 740 896.2 with a mailing date of Sep. 21, 2020.
Xiaowen Huang et al., "On-Si te Formation of Emulsions by Controlled Air Plugs",Small, vol. 10, No. 4, Feb. 1, 2014 (Feb. 1, 2014), pp. 758-765.
Extended European Search Report for European Patent Application No. 16 74 0896, with a mailing date of Jun. 6, 2018.

* cited by examiner

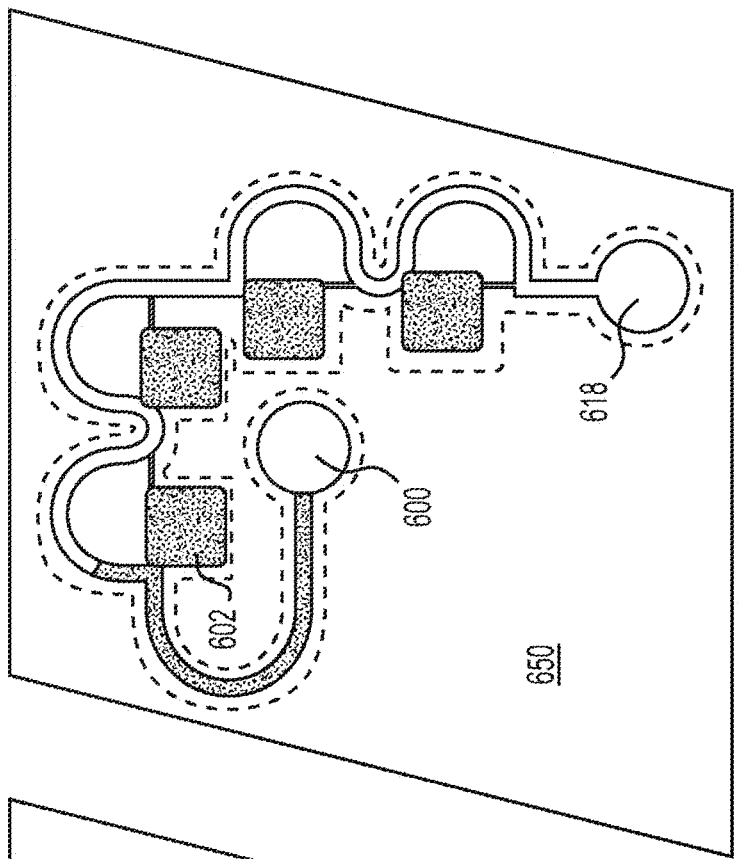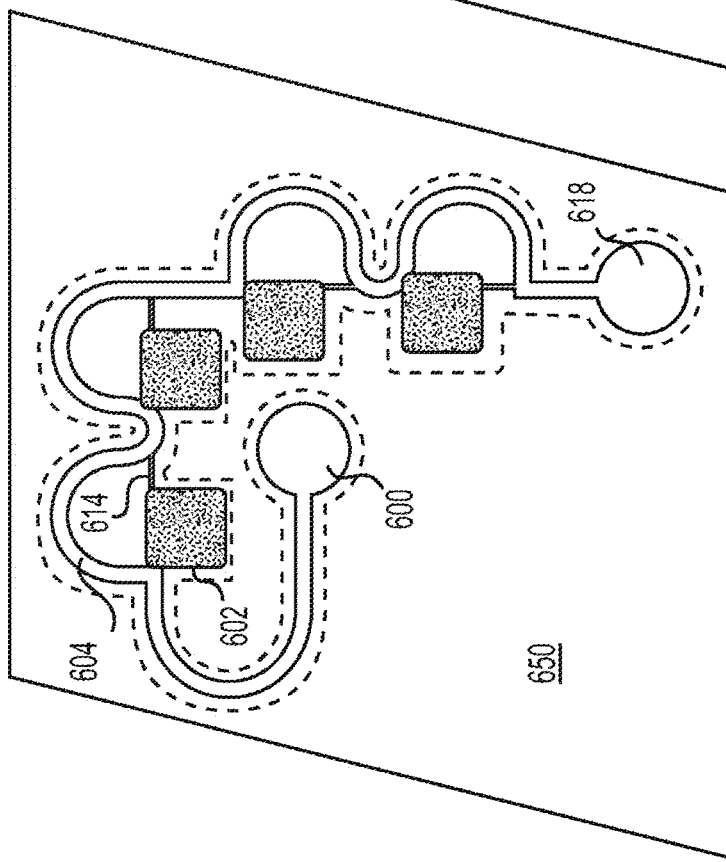

| CELL COUNTING EXPERIMENTS | HEMOCYTOMETER | CHIP W/O TRYPAN BLUE | CHIP WITH TRYPAN BLUE |
|---|---|---|---|
| TEST 1 | $6.7 \times 10^6$ CELLS/ml | $6.65 \times 10^6$ CELLS/ml | X |
| TEST 2 | $4.7 \times 10^6$ CELLS/ml | X | $5.01 \times 10^6$ CELLS/ml |

*FIG. 9A*

| PARAMETERS | HEMOCYTOMETER | NEOPLATE |
|---|---|---|
| TIME TO LOAD CELLS | 45-60 SEC | 5-6 SEC |
| TIME TO COUNT CELLS | 5-6 MIN | 1.5-2 MIN |
| TOTAL TIME TO GET CELL COUNT | 7-8 MIN | 2-2.5 MIN (70-75% REDUCTION IN TIME) |
| DISTRIBUTION OF CELLS IN 4 QUADRANTS | UNEVEN | EVEN |
| EASE OF HANDLING | NOT EASY | VERY EASY |
| HOW DELICATE? | VERY DELICATE | ROBUST |
| REUSABILITY | REUSABLE | REUSABLE |
| OTHER FUNCTIONS | NO | CAN BE USED FOR CELL BASED EXPERIMENTS SUCH AS ASSAY, STAINING ETC. |

*FIG. 9C*

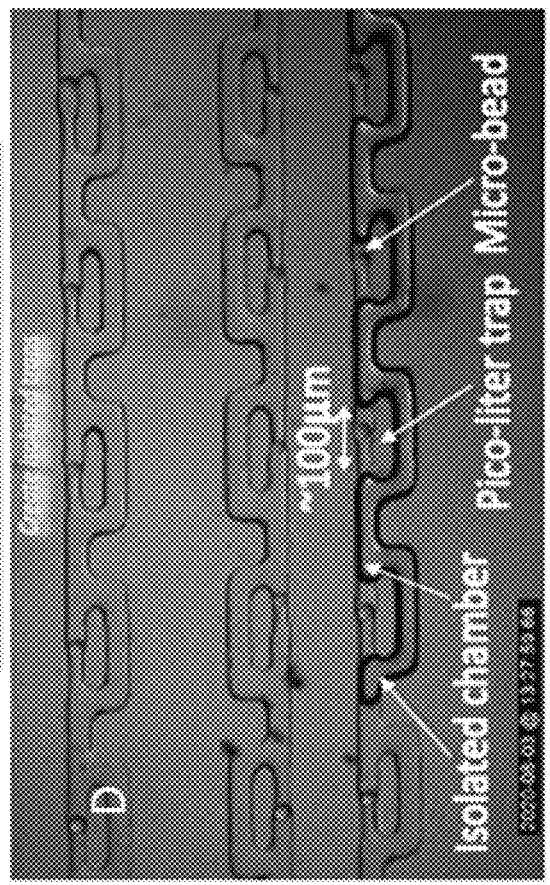
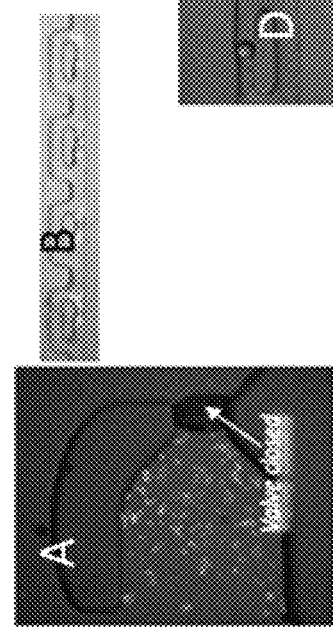
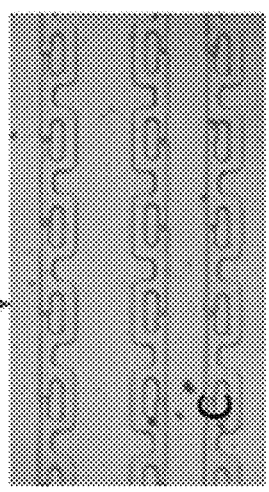
*FIG. 13A*    *FIG. 13B*
*FIG. 13C*    *FIG. 13D*

2200

```
┌─────────────────────────────────────┐
│ Introduce simultaneously a first    │
│ fluid into a first                  │——— 2201
│ inlet and a second fluid into a     │
│ second inlet.                       │
└─────────────────────────────────────┘
                  │
                  ▼
┌─────────────────────────────────────┐
│ Cause the first and second fluids   │
│ to enter into                       │——— 2202
│ a bypass channel.                   │
└─────────────────────────────────────┘
                  │
                  ▼
┌─────────────────────────────────────┐
│ Cause the first and second fluids   │
│ to enter into                       │——— 2203
│ a fluidic trap.                     │
└─────────────────────────────────────┘
                  │
                  ▼
┌─────────────────────────────────────┐
│ Cause the first and second fluids   │
│ to be mixed                         │——— 2204
│ in the fluidic trap.                │
└─────────────────────────────────────┘
```

*FIG. 15*

MICROFLUIDIC SERIAL DILUTION PLATFORM BASED WELL-PLATE USING AN OIL-FREE IMMISCIBLE PHASE DRIVEN BY MANUAL OR ELECTRONIC PIPETTORS

CROSS REFERENCE TO RELATED APPLICATIONS

This application is a continuation-in-part (CIP) application of U.S. application Ser. No. 15/005,341, filed on Jan. 25, 2016, which claims priority of U.S. Provisional Application Ser. No. 62/107,132, entitled "A MICROFLUIDIC SERIAL DILUTION PLATFORM BASED WELL-PLATE USING AN OIL-FREE IMMISCIBLE PHASE DRIVEN BY MANUAL OR ELECTRONIC PIPETTORS," and herein incorporated by reference in its entirety.

BACKGROUND

Currently, microfluidic devices that can achieve storage of nano-pico liter volumes of droplets use either upstream mechanisms (such as T-junction or Y-junctions) or external force driven methods (electric, magnetic or acoustic). See, for example, the following published applications and patents US PGPUB 20070195127, WO 2010111231, U.S. Pat. Nos. 723,826, 7,708,949, EP2364774, U.S. Pat. No. 8,765,485 and WO2006096571. Passive methods include the fragmentation of a long slug of fluid into droplets in a hydrophobic microfluidic network by using an immiscible phase (usually oil). In order to use this passive method, the current state of the art requires that the traps be pre-filled with the immiscible oil-phase. This creates a capillary plug in the constriction that immediately follows the trap to ensure that the droplets do not escape from the traps and to accomplish uniform droplet trapping. See, for example, the following published applications and patents: U.S. Pat. No. 8,592,221, CA2521862 and WO2012154688.

Once these droplets are trapped in these pre-defined sites, current methods used to achieve serial dilution of these stored droplets rely on coalescence between the diluting stream and the trapped droplets when these two components meet in the larger entrance channel of the trap. This causes the composition of the diluting plug to be altered which in turn can cause adverse reactions in this plug as it coalesces with droplets further downstream in the network.

There are a number of disadvantages of the above-described current techniques. For example, current techniques require precise fluidic control and additional external manifolds and controls. The immiscible oil phase (a contaminant in some processes) is required in the traps prior to droplet trapping to prevent drops from escaping from the traps. Additionally, the dilution mechanism of current methods can cause contamination of downstream traps in the network. Moreover, the non-uniform trapping of particles (e.g., cells) in traps in methods that use the fragmentation of a long fluidic slug.

SUMMARY

Described herein are embodiments of a microfluidic serial dilution platform based well-plate using an oil-free immiscible phase driven by manual or electronic pipettors that overcomes the defects of the prior art. These and other advantages are achieved by a microfluidic serial dilution platform based well-plate using an oil-free immiscible phase driven by manual or electronic pipettors. The well-plate includes a plurality of fluidic traps, a plurality of hydrophilic capillary constriction channels and a plurality of bypass channels. Each of the plurality of bypass channels is associated with one of the plurality of fluidic traps, each of the plurality of hydrophilic capillary constriction channels is associated with one of the plurality of fluidic traps, and each of the plurality of fluidic traps is associated with one of the plurality of bypass channels and one of the plurality of hydrophilic capillary constriction channels. The well-plate further includes an inlet, an outlet, and a main channel with a plurality of portions that connects the inlet to the plurality of fluidic traps, associated hydrophilic capillary constriction channels and associated bypass channels, and the outlet.

These and other advantages are also achieved by a microfluidic serial dilution platform based well-plate using an oil-free immiscible phase driven by manual or electronic pipettors. The well-plate includes a plurality of fluidic traps, a plurality of hydrophobic capillary constriction channels, and a plurality of bypass channels. Each of the plurality of bypass channels is associated with one of the plurality of fluidic traps, each of the plurality of hydrophobic capillary constriction channels is associated with one of the plurality of fluidic traps, and each of the plurality of fluidic traps is associated with one of the plurality of bypass channels and one of the plurality of hydrophobic capillary constriction channels. The well-plate also includes an inlet, an outlet, and a main channel with a plurality of portions that connects the inlet to the plurality of fluidic traps, associated hydrophobic capillary constriction channels and associated bypass channels, and the outlet.

BRIEF DESCRIPTION OF THE DRAWINGS

Embodiments of a system and method for network data characterization and/or classification are understood and described in conjunction with the following drawings, wherein:

FIGS. 6A-6B are diagrams illustrating a hydrophobic operation of a hydrophobic embodiment of the microfluidic serial dilution platform based well-plate using an oil-free immiscible phase driven by manual or electronic pipettors, particularly a serial dilution process of the operation.

FIG. 9A is a table illustrating results of an experiment using a hydrophobic embodiment of the microfluidic serial dilution platform based well-plate using an oil-free immiscible phase driven by manual or electronic pipettors as a hemocytometer.

FIG. 9C is a chart illustrating advantages of hydrophobic embodiment of the microfluidic serial dilution platform based well-plate using an oil-free immiscible phase driven by manual or electronic pipettors versus a standard hemocytometer.

FIGS. 13A-13D show shown are embodiments on in-vitro screening of cells against drugs.

FIG. 15 shows a flowchart for a method of operating a microfluidic serial dilution platform based well-plate of the disclosed invention.

DETAILED DESCRIPTION

Described herein are embodiments of a microfluidic serial dilution platform based well-plate using an oil-free immiscible phase driven by manual or electronic pipettors. Embodiments overcome the problems described above. For example, embodiments provide a passive method based device for storage and serial dilution of fluids in a microfluidic storage network. Embodiments include a microfluidic platform based well-plate using an oil-free immiscible phase driven by manual or electronic pipettors. Embodiments provide a novel mechanism for storage and serial dilution of droplets in a hydrophilic microfluidic device using conventional pipetting system.

Embodiments overcome the problems of the prior art. For example, by using an air-based immiscible phase for droplet trapping, embodiments eliminate the possibility of a reaction between typically-used oil-based immiscible phases and trapped fluid. Likewise, the novel serial dilution by the formation of micro-droplets in the network provided by embodiments prevents the composition of the diluting slug from being changed. Additionally, the elimination of precise fluidic control allows the storage and dilution of droplets in the network to be accomplished by conventional pipetting systems. The incorporation of these networks into a well-plate based device that integrates with multi-head robotic and manual pipettors eliminates the need for any additional capital equipment. The trapping and dilution is performed in a completely passive manner (without use of electric or magnetic fields), reducing the cost of the device. Embodiments provide a similar or higher throughput compared to currently available robotic high-throughput screening systems. Moreover, embodiments provide the ability to remove fluids trapped in square hydrodynamic traps with a reversal of the direction of flow in one step without the formation of emulsions. Embodiments also enable uniform trapping of cells and other particles suspended in a fluid over the entire network of traps. This is particularly important in cell-based screening studies.

Figure 1A:
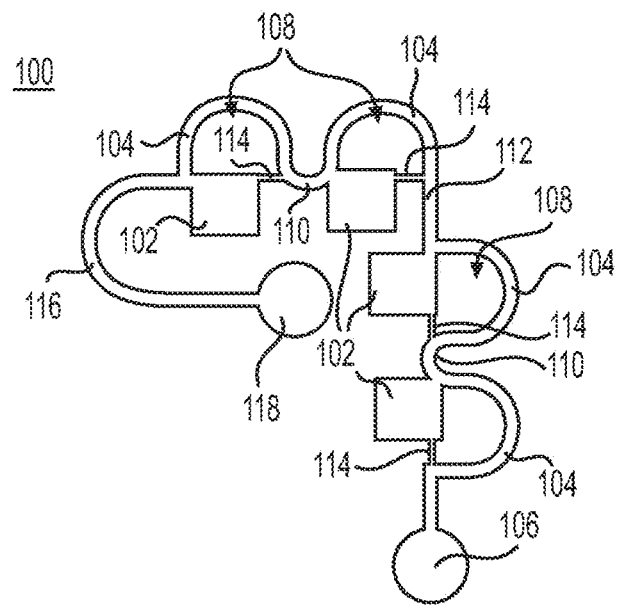
FIGS. 1A-1D are diagrams illustrating a hydrophilic embodiment of a microfluidic serial dilution platform based well-plate using an oil-free immiscible phase driven by manual or electronic pipettors.
Figure 1B:
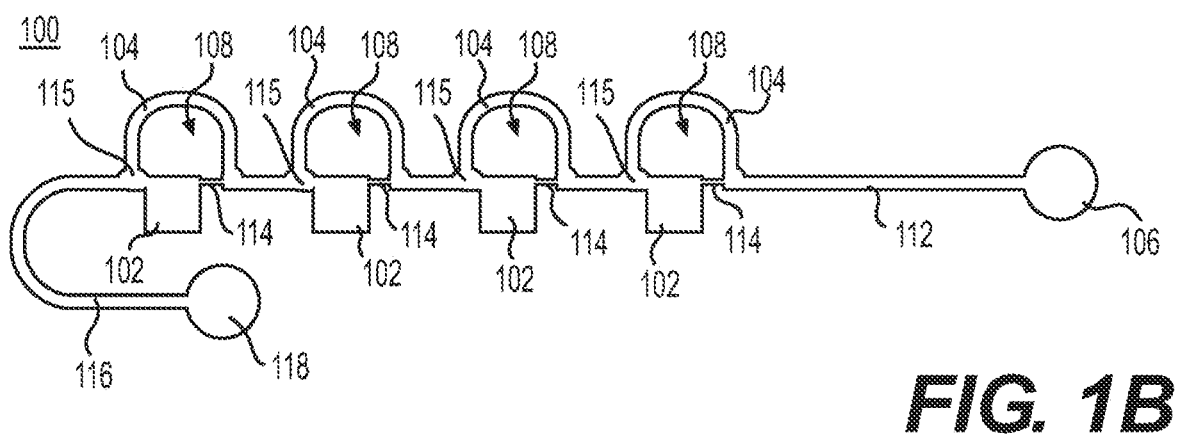
Figure 1C:
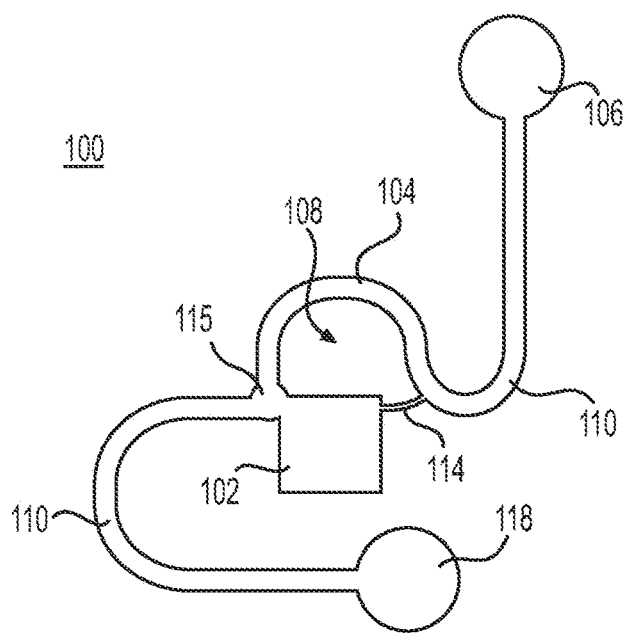
Figure 1D:
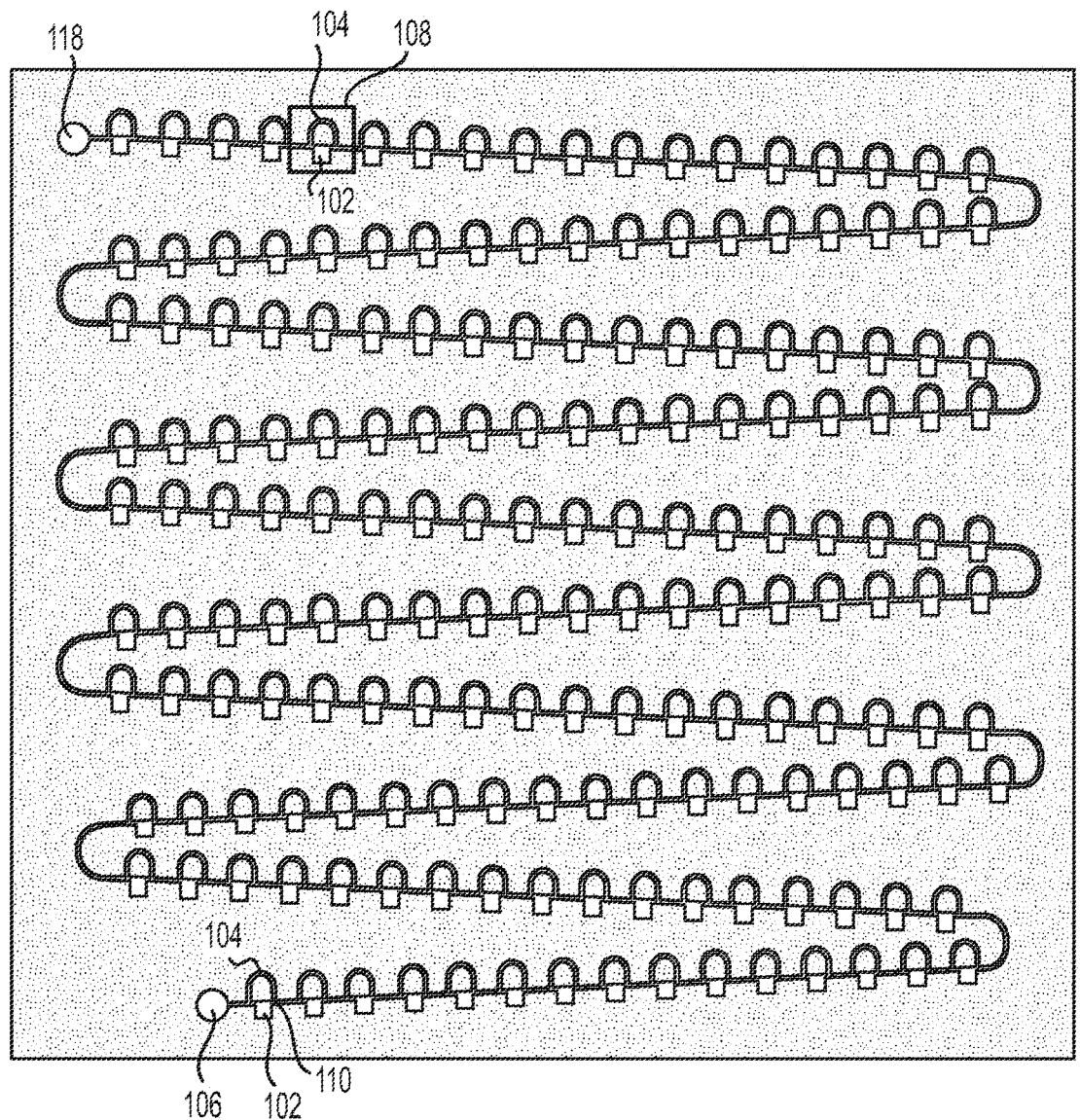

With reference now to FIGS. 1A-D, shown are four hydrophilic embodiments of a microfluidic serial dilution platform based well-plate 100 using an oil-free immiscible phase driven by manual or electronic pipettors. Each embodiment of well-plate 100 includes a network of one or more fluidic traps 102. The drawings shown in FIGS. 1A-1C illustrate only a portion a well-plate and the network of fluidic traps 102 on the well-plate. FIG. 1A shows an embodiment of well-plate 100 with a parallel network of four (4) traps 102 with associated bypass channels 104. In an actual implementation, the well-plate with such network may include multiple repeating networks configured as such. FIG. 1B shows an embodiment of well-plate 100 with a series network of four (4) traps 102 with associated bypass channels 104. In an actual implementation, the well-plate with such network may include multiple repeating networks configured as such. FIG. 1C shows an embodiment of well-plate 100 with a single trap 102 with associated bypass channels 104. In an actual implementation, the well-plate may include repeating single trap networks. FIG. 1D shows an embodiment with 176 traps 102 with associated bypass channels 104 connected in a series network. This last embodiment illustrates that the number of traps can be chosen and configured to meet requirements based on the application. The microfluidic serial dilution platform based well-plate designs shown herein may be situated on a chip or other suitable substrate. The well-plates may be made from, for example, poly dimethyl siloxane (PDMS), cyclic olefin copolymer (COC), poly carbonate (PC), or similar materials.

With continuing reference to FIG. 1A, an embodiment includes a fluidic inlet channel 106 connected to traps 102 and associated bypass channels 104 (each trap 102 and bypass channel 104 together forming a well 108) in parallel arrangement. Fluidic inlet channel 106 includes an interface for pipettor, pipette or other fluid driving mechanism. The embodiment shown further includes main channel 110, including straight channel portion 112, connecting individual wells 108 together in parallel circuit as shown, and hydrophilic capillary constriction channels 114 with, e.g., 40 µm width (small constriction inlet) connecting main channel 110 directly to traps 102. In embodiments, square fluidic traps 102 have, e.g., 1 mm×1 mm sides and bypass channels 104 have, e.g., 200 μm width. In embodiments, main channel extension 116 connects traps 102 to fluidic outlet 118. Each trap 102 is an enclosed chamber with openings where main channel 110 and hydrophilic capillary constriction channels 114 connect with trap 102. Furthermore, while the traps 102 shown in FIGS. 1A-1D are square traps, embodiments may include any variety of shaped traps, including circular or semi-circular traps. Not shown in FIGS. 1A-1D are covers that cover the entire well-plate and the network of fluidic traps 102 on the well-plate (see FIG. 10 for an example of a cover). The cover encloses each trap 102, as well as the various channels, creating the enclosed chamber. In a hydrophilic embodiment, such as describe here with reference to FIGS. 1A-1D the cover is also hydrophilic in nature.

With reference again to FIG. 1B, an embodiment includes fluidic inlet channel 106 with an interface for pipettor, pipette or other fluid driving mechanism, straight channel portion 112 of main channel 110 extending from inlet 106 and, with rest of main channel 110, connecting inlet 106 to fluidic traps 102 and associated bypass channels 104 (together forming a well 108) in a series circuit with each other, and hydrophilic capillary constriction channels 114 with, e.g., 40 μm width (small constriction inlet), connecting main channel 110 directly to traps 102. Bypass channels 104 may be fabricated with a, e.g., 200 μm width, and fluidic traps 102 may be fabricated as square, e.g., 1 mm×1 mm, fluidic traps 102. Embodiment may include enlarged main channel portions 115 to optimize a reduction of air invading into the fluidic trap 102 and main channel extension 116 connecting traps 102 to fluidic outlet 118.

With reference again to FIG. 1C, shown is an embodiment with a fluidic inlet channel 106 with an interface for pipettor, pipette or other fluid driving mechanism, main channel 110 connecting fluidic trap 102 to inlet, hydrophilic capillary constriction channel 114 with, e.g., 40 μm width (small constriction inlet), connecting main channel 110 to trap 102, enlarged channel 115 to minimize invasion of air into the fluidic trap 102, and main channel 110 connecting well or trap 102 to fluidic outlet 118.

With reference again to FIG. 1D, shown is 176 fluidic traps 102 connected in series from fluidic inlet 106 to fluidic outlet 118. As above, each trap 102 and bypass channel 104 together form well 108 and adjacent trap 102 and bypass channel 104 combinations are connected by main channel 110 and various portions or extensions thereof.

Figure 1E:
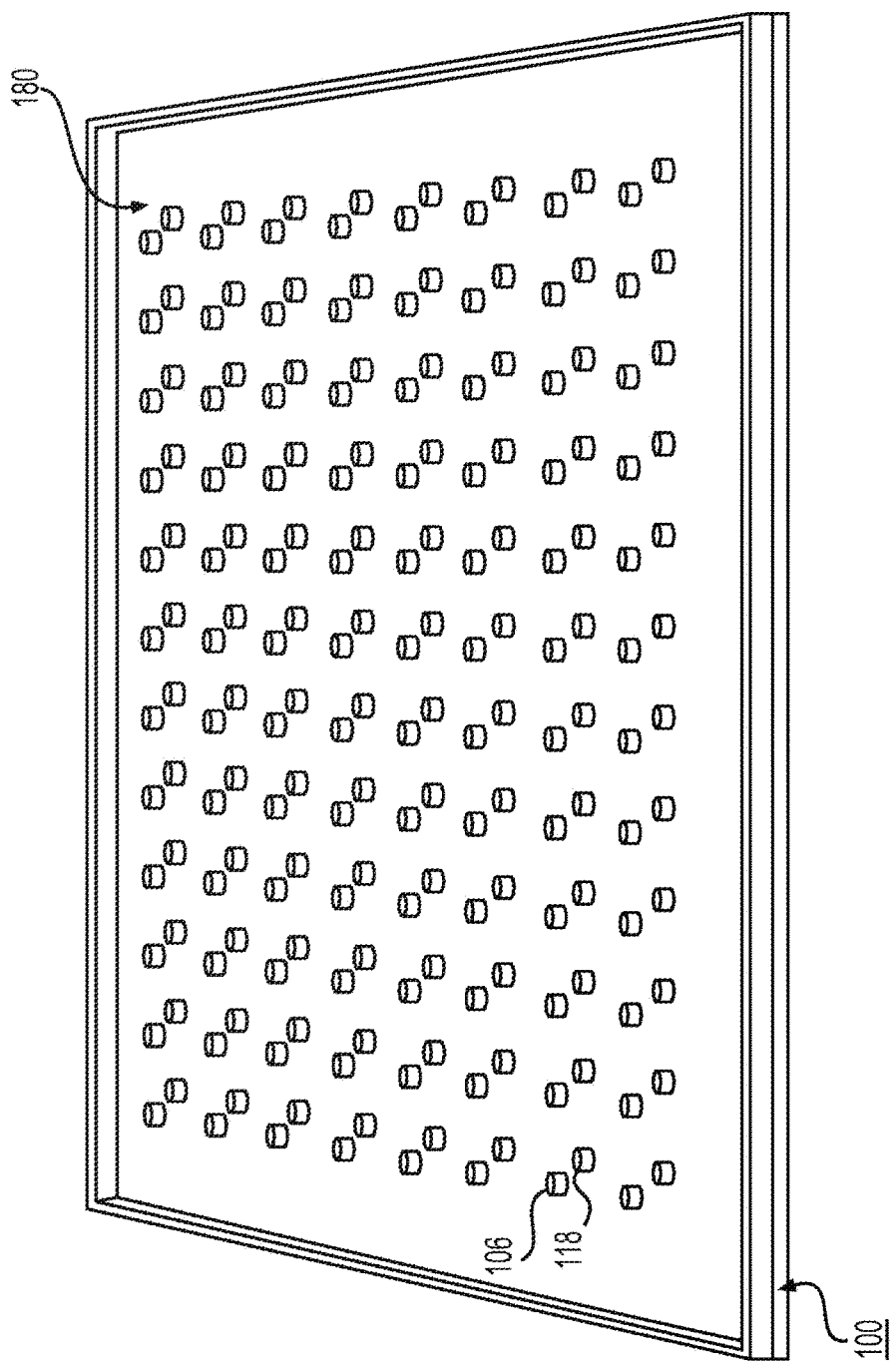
FIG. 1E is a diagram illustrating an entire well-plate, with cover, that includes an embodiment of a microfluidic serial dilution platform using an oil-free immiscible phase driven by manual or electronic pipettors.

With reference now to FIG. 1E, shown is an entire well-plate 100 with a uniform network of ninety-six fluidic traps. Visible is cover 180, fluidic inlets 106 and fluidic outlets 118 for each fluidic trap network. Fluidic inlets 106 and fluidic outlets 118 extend through cover 180.

Figure 2A:
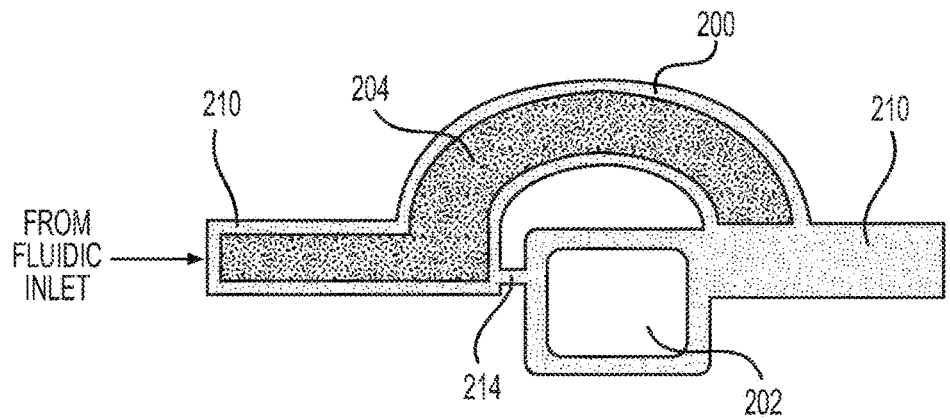
FIGS. 2A-2C are diagrams illustrating a hydrophilic operation of a hydrophilic embodiment of the microfluidic serial dilution platform based well-plate using an oil-free immiscible phase driven by manual or electronic pipettors, particularly a fluid trapping process of the operation.
Figure 2B:
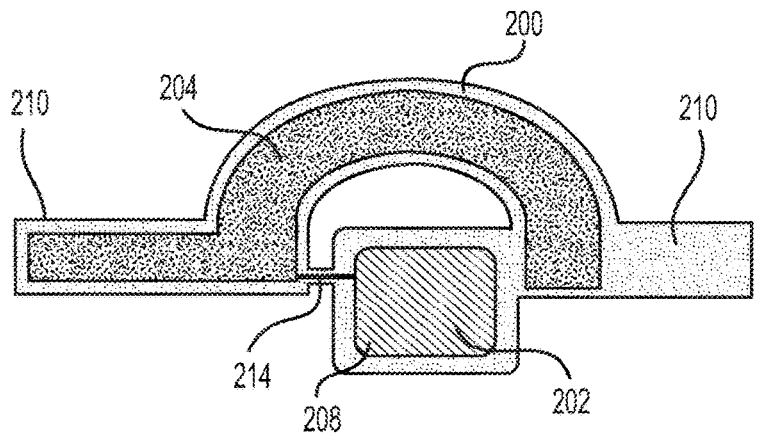
Figure 2C:
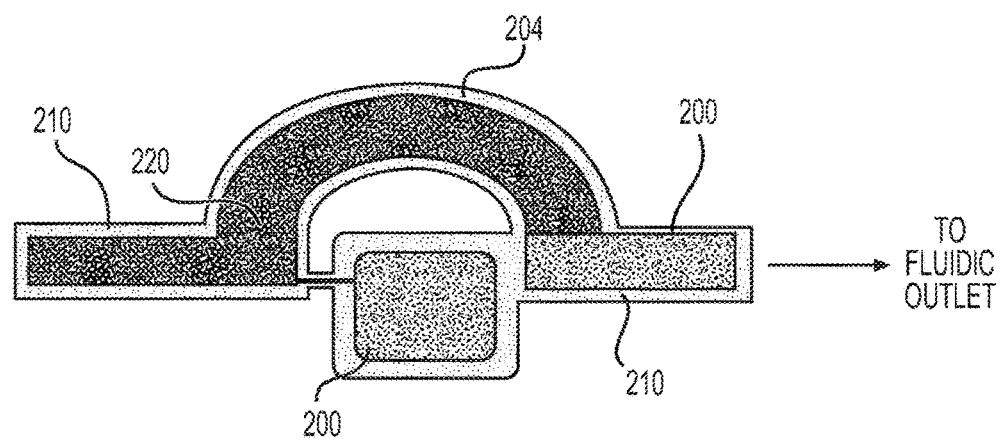

With reference now to FIGS. 2A-2C shown are schematic diagrams illustrating a fluid trapping process using embodiments of a microfluidic serial dilution platform based well-plate using an oil-free immiscible phase driven by manual or electronic pipettors. Shown in FIG. 2A, fluid 200 first enters the bypass channel 204, through main channel 210 from direction of fluidic inlet (not shown), enhancing or increasing the hydrodynamic resistance in the bypass channel 204, and stops at the larger constriction of the main channel 210 and unfilled fluidic square trap 202. Also shown in FIG. 2A is unfilled hydrophilic capillary constriction channel 214.

With reference now to FIG. 2B, fluid 200 is shown now filling the fluidic square trap 202 through the smaller constriction (hydrophilic capillary constriction channel 214) connected upstream to square trap 202. Fluid 200 in bypass channel 204 now stops at mouth of the trap 202.

With reference now to FIG. 2C, air 220 is then passed through the network of fluidic traps 202. The air 220 passes through bypass channel 204, removing remaining excess fluid 200 from the bypass channel 204 into main channel 210 and leaving a fragmented droplet of fluid 200 trapped in the hydrodynamic trap 202. Air 220 will continue to pass through main channel 210 to next well (not shown), removing excess fluid 200 from bypass channel of next well, and so on through network of traps 202 towards fluidic outlet (now shown).

Figure 3:
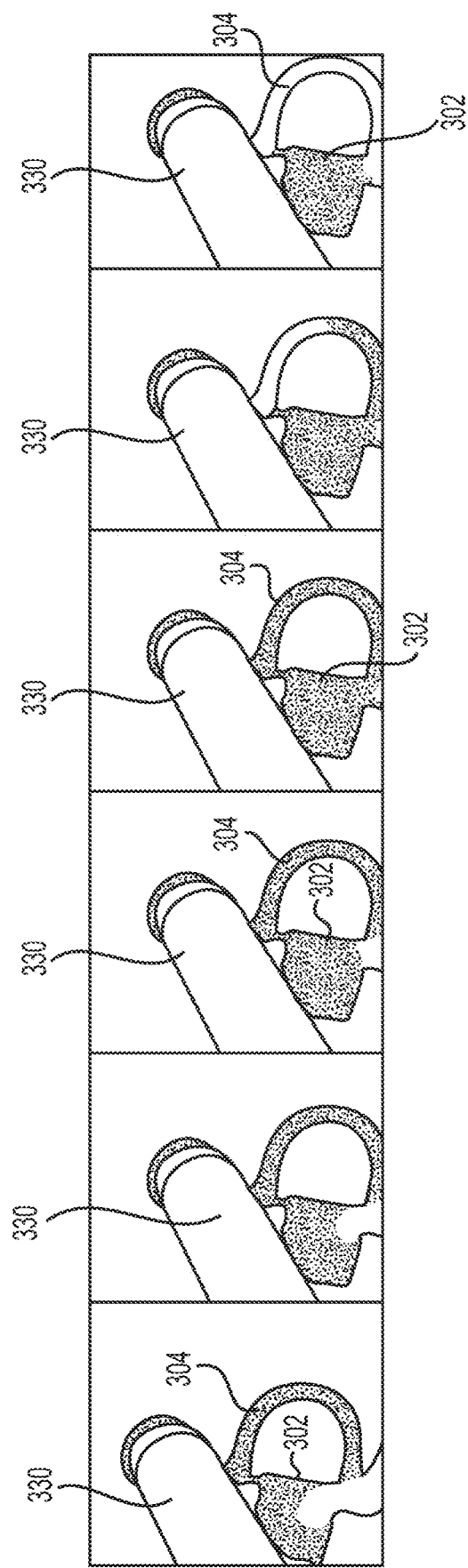
FIG. 3 is a series of images illustrating the fluid trapping process of an embodiment of the microfluidic serial dilution platform based well-plate using an oil-free immiscible phase driven by manual or electronic pipettors.

With reference now to FIG. 3, shown are a series of images illustrating the trapping process described above and illustrated in FIGS. 2A-2C. With reference to FIG. 3, shown are a series of micrograph images 1-6 of the series of events that leads to the fragmentation of the long fluid slug and the trapping of fluid in the square trap. Pipettor 330 connected to fluidic inlet channel (e.g., see fluidic inlet channel 106 in FIGS. 1A-D) with an interface for pipettor 330, pipette or other fluid driving mechanism is shown in these images.

With reference now to FIGS. 4A-D, shown are schematic diagrams illustrating a serial dilution process using an embodiment of microfluidic serial dilution platform based well-plate using an oil-free immiscible phase driven by manual or electronic pipettors. Steps shown in FIGS. 4A-4D take place after the fluid trapping process described above. Together, the fluid trapping process and serial dilution process, shown in FIGS. 2A-2C and 4A-4D, comprise a significant portion of the operation of the microfluidic serial dilution platform based well-plate using an oil-free immiscible phase driven by manual or electronic pipettors.

Figure 4A:
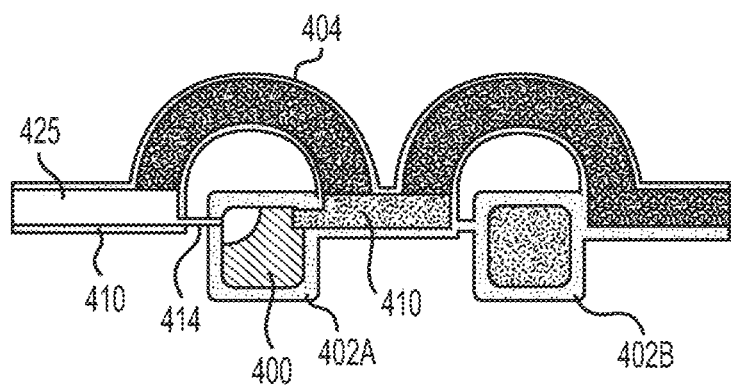
FIGS. 4A-4D are diagrams illustrating a hydrophilic operation of a hydrophilic embodiment of the microfluidic serial dilution platform based well-plate using an oil-free immiscible phase driven by manual or electronic pipettors, particularly a serial dilution process of the operation.

With reference to FIG. 4A, diluting stream or fluid (white) 425 first displaces air 420 and enters the main channel 410, then enters the constriction (hydrophilic capillary constriction channel) 414 upstream of the network, invading a part of a first fluid-filled trap 402A, diluting the fluid 400 in the trap 402. Fluid 400 is ejected from the trap 402A into the main channel 410 due to the displacement of fluid 400 from the trap 402A by the diluting fluid 425. The portion of fluid 400 that exited the first trap 402A now enters the second trap 402B and causes a portion of fluid 400 to leave the second trap 402B.

Figure 4B:
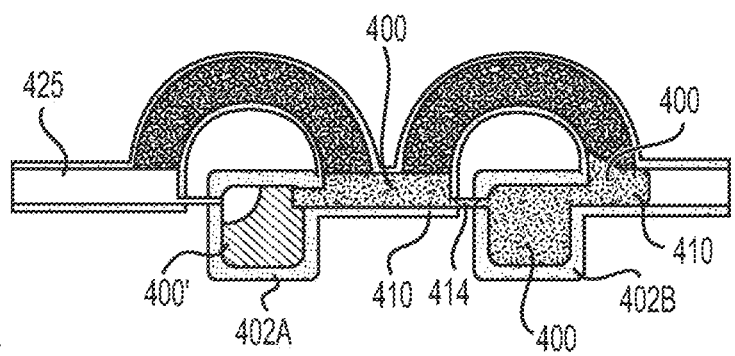

With reference to FIG. 4B, shown is trap 402A filled with diluted fluid 400', ejected fluid 400 in main channel 410, ejected fluid 400 from first trap 402A that has entered second trap 402B, connected in series, through hydrophilic capillary constriction channel 414 of second trap 402B, and fluid ejected from second trap 402B into main channel 410. As an increasing amount of diluting fluid 425 enters the upper section of the first trap 402A a portion of the diluting stream 425 now enters the second trap 402B and a series of micro-droplets are formed that enter successive traps causing a serial dilution.

Figure 4C:
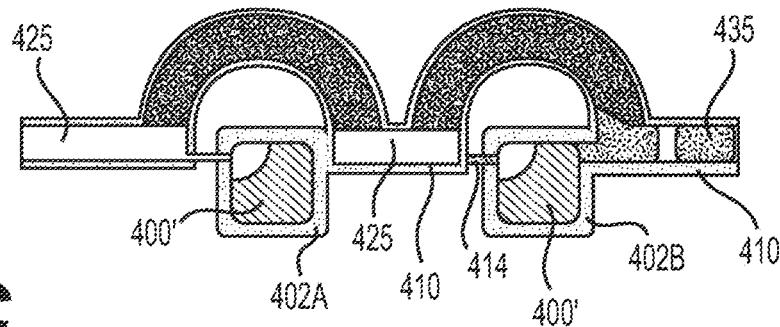

With reference to FIG. 4C, shown is diluted fluid 400' in first trap 402A, diluting fluid 425 filling upper section of first trap 402A and entering second trap 402B, diluting fluid 425 filing capillary section 414 of the second trap 402B, and as air is injected into device following the diluting plug, causing fluidic droplets 435 in air phase to form. As air is pumped into the channel 410 following the diluting stream, excess diluting fluid 425 is carried away from the channel into the outlet.

Figure 4D:
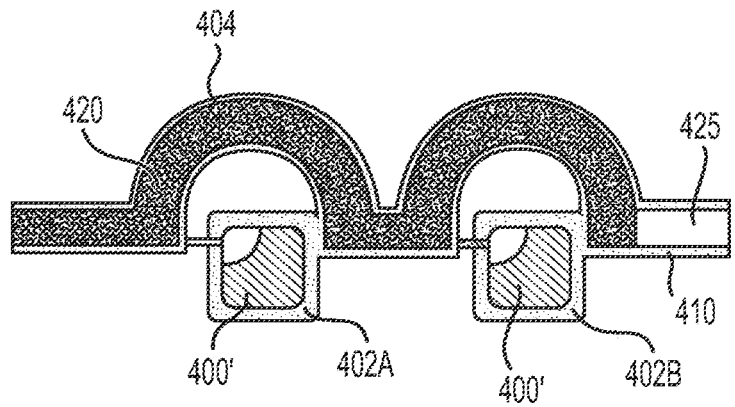

With reference to FIG. 4D, shown is air-filled bypass channel 404 as air 420 is driven into bypass channels 404 after the diluting plug, the diluted fluid 400' in first trap 402A, the diluted fluid 400' in second trap 402B and main channel 410 with excess fluid 425 flushed out with air phase.

Figure 5:
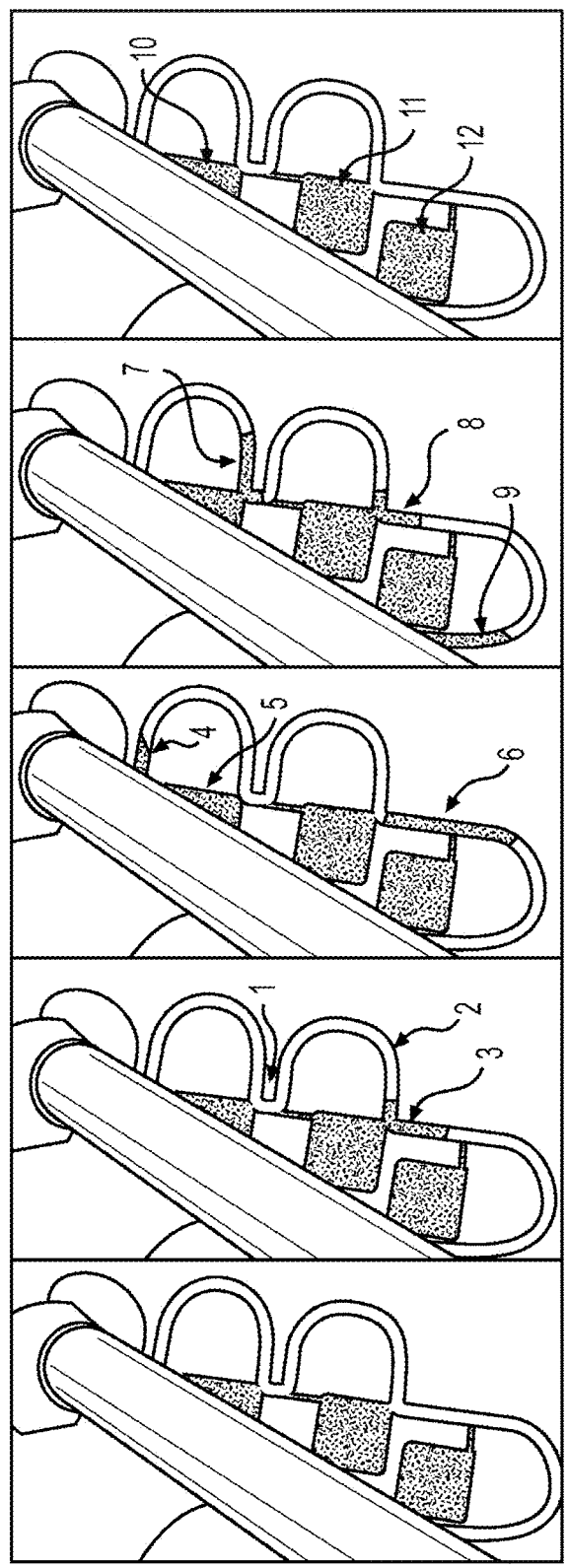
FIG. 5 is a series of images illustrating the serial dilution process of an embodiment of the microfluidic serial dilution platform based well-plate using an oil-free immiscible phase driven by manual or electronic pipettors.

With reference now to FIG. 5 shown are a series of images illustrating the serial dilution process described above with reference FIGS. 4A-4D. Shown in FIG. 5, are five (5) micrograph images of the series of events that leads to serial dilution of the trapped droplets. In image 2, ejected fluid from first trap enters 1 second trap connected in series, bypass channel 2 is filled with air, and fluid is ejected 3 from second trap. In image 3, diluting fluid enters 4 capillary section of first trap, fluid in first trap 5 is now diluted, ejected fluid from second trap forms a fluid drop 6 in air phase. In image 4, diluting fluid fills upper section of first trap 7 and is subsequently ejected, diluting fluid fills upper section of second trap 8 and is ejected from second trap into main channel and ejected micro-droplet 9 from second trap is shown in main channel. In image 5, first trap 10 has the highest amount of diluting fluid, second trap 11 has a comparatively lower amount of diluting fluid compared to first trap and a third trap 12 has the lowest amount of diluting fluid compared to first trap and second trap.

Embodiments enable dilution of different magnitudes carried out in a trapping network. For example, embodiments enable cell cultures to be carried out in the traps, such as breast cancer cells cultures in a matrigel environment in the traps. Embodiments provide a new method for the trapping and dilution of nano to pico liter droplets stored in microfluidic networks. By using a novel design and employing hydrophilic square channels the fluid is pumped in through capillary action and the applied pressure drop of a pipettor. The fluid is driven into the channel in the direction where the smaller constriction of the trap is upstream (as opposed to the conventional system where fluid enters the trap through the larger constriction). The fluidic slug then fills the entire trap by flowing through this constriction (see FIGS. 2 and 3). Consecutive traps in the network are also filled in this manner. Air is then used as the immiscible phase to fragment the long fluidic slug and remove excess fluid contained in the bypass channels.

Consequently, the method utilized by embodiments described herein do not require an immiscible oil phase which can cause adverse results in some applications, although if required an immiscible oil phase can also be used to fragment the fluidic slug in the trap by flowing it through the network at a lower pre-defined flow rate.

Embodiments of the method utilized by embodiments described herein allows for the slug to be trapped and fragmented using larger pressure drops (which are typical for off-the shelf pipetting systems) compared to currently available solutions that require optimization of flow rates or additional external pumping systems (such as syringe pumps).

Embodiments also dilute fluids stored in the traps using a novel dilution method that produces fluidic drops in-air, in-situ in the device. This method with optimization can prevent cross-contamination between compositions of fluids in the various stationary traps. Embodiments of the device described herein can also be used for the three-dimensional culture of cells in the hydrodynamic traps using an appropriate polymer matrix. These cultured cells can then be serially diluted and screened against drugs in an HTS fashion.

In embodiments described herein, a hydrophilic channel microfluidic based network with square (or other shaped) storage traps (see FIGS. 1A-1D) to store and dilute nano- liter droplets. These droplets are produced in-situ in these square traps by flowing a fluidic slug through the fluidic network in a direction where with the smaller capillary junction is upstream of the large entrance channel at the traps. This injection of fluid into the channels is achieved at high flow rates using a commercially available pipetting system. This is followed by fragmenting the long slug of fluid using an immiscible air-phase that removes excess fluid from the channels causing nano to pico liter droplets of fluid to be contained in the square traps (see FIGS. 2 and 3). The need for an immiscible oil-phase is, therefore, completely eliminated.

Embodiments of the method for dilution causes the diluting stream to directly enter into part of the square (or other shaped) trap (amount can be varied based on volume, size of trap and flow rate of the diluting stream) (see FIGS. 4 and 5).

The injection of the diluting stream into the trap causes part of the reagent in the trap to be displaced, which in turn causes the formation of a fluid droplet in the air filled channels (see FIG. 4). This droplet then enters the second trap (where composition is the same as first trap) and causes another fluid-air drop to be produced (see FIG. 5). This mechanism, therefore, can produce serial dilutions without causing contamination of the diluting stream or of the reagents in the traps downstream. Both the trapping and serial dilution of the droplets in the device are performed using conventional pipetting systems without the need for precise fluid control or lower flow rates.

In another embodiment, only the cover of the microfluidic structure is chosen to be hydrophilic in nature. With reference now to FIGS. 6A-6B, shown are schematic diagrams that illustrate trapping using this such an embodiment. These diagrams again illustrate only a portion of a well-plate and a portion of the network of traps on the well-plate. The fluid is first trapped by injecting it into the channel towards the larger mouth of the hydrodynamic trap that is filled initially with air. The channels are hydrophobic while the base cover used to enclose these channels is hydrophilic in nature. The fluidic slug fills the trap while not entering the hydrophobic capillary section that has a larger hydrodynamic resistance than the fluidic trap and is filled with air. This capillary section filled with air, therefore, acting as an air valve. Once the trap is completely filled, the hydrodynamic resistance of the trap is enhanced and excess fluid from the trap then moves into the bypass channel. This fluid subsequently enters other traps in the network and fills them in the same method as described previously.

The fluids that are filled in these traps can then be diluted by coalescence between the diluting and trapped fluid. See for example US Patent No. WO2012154688 A2. This is depicted in FIG. 6B.

With reference again to FIG. 6A, shown is an outlet for fluid 618, fluid filled first hydrodynamic trap 602, bypass channel of fluidic network 604, capillary section of hydrodynamic trap filled with air 614, inlet for fluid driven by pipette or other fluid driving mechanism 606, structure of the fluidic network that is hydrophobic in nature and base 650 of the fluidic network, that is used to cover the hydrophobic structure, which is hydrophilic in nature.

With reference again to FIG. 6B, shown is an outlet for fluid 618, diluted filled first hydrodynamic trap 602, diluting fluid injected from the inlet 606, diluting fluid coalescing with fluid trapped in hydrodynamic trap 602, inlet for fluid driven by pipette or other fluid driving mechanism 606, structure of the fluidic network that is hydrophobic in nature and hydrophilic base 650 of the fluidic network that is used to cover the microfluidic hydrophobic structure. Note, the various features described herein with reference to the hydrophilic embodiments (see FIGS. 1A-5, 10A-10B) may be incorporated into the hydrophobic embodiment described in FIGS. 6A-6B.

Figure 7A:
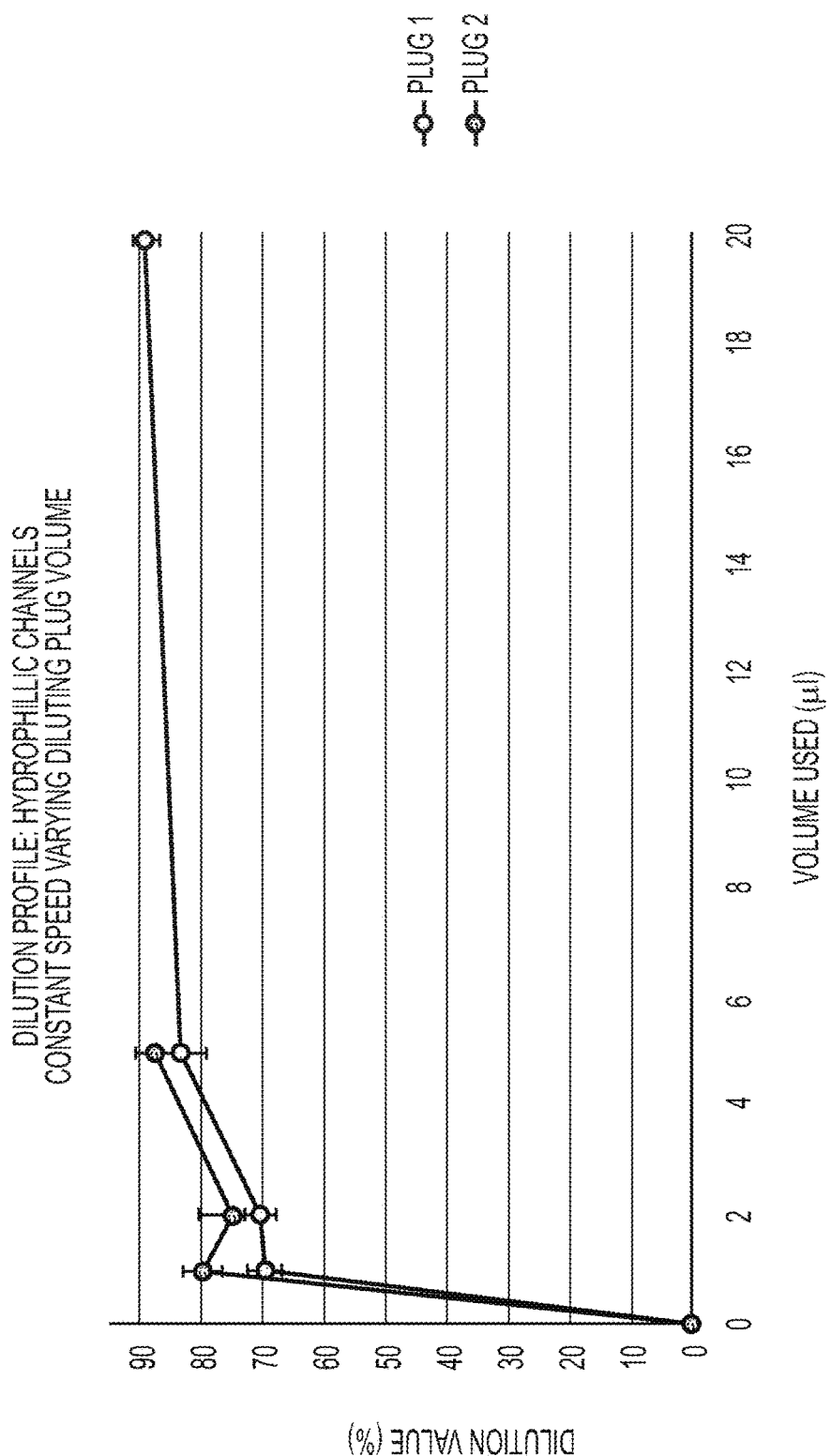
FIGS. 7A-7C are graphs illustrating data from dilutions using a hydrophilic embodiment of the microfluidic serial dilution platform based well-plate using an oil-free immiscible phase driven by manual or electronic pipettors.
Figure 7B:
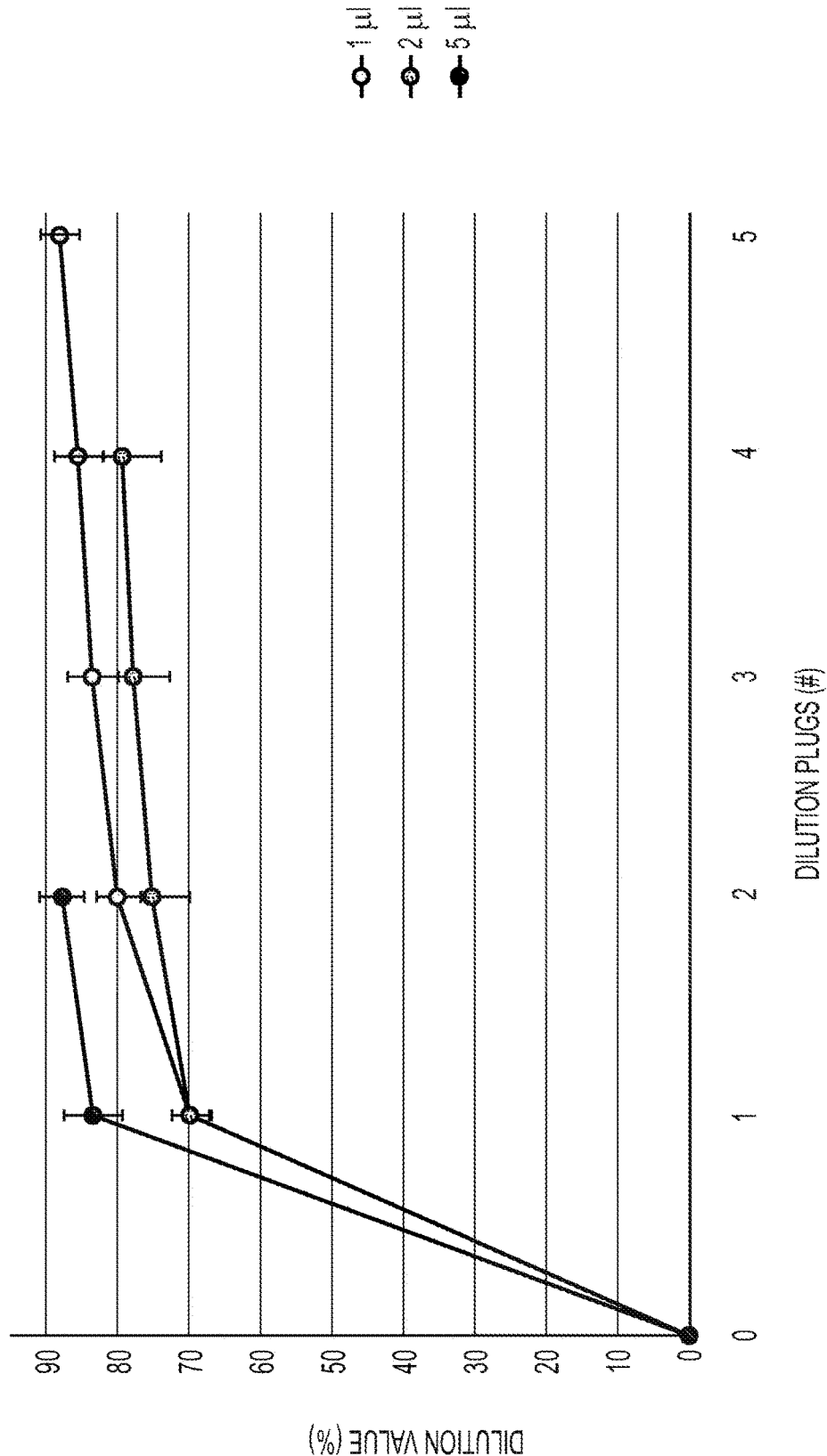
Figure 7C:
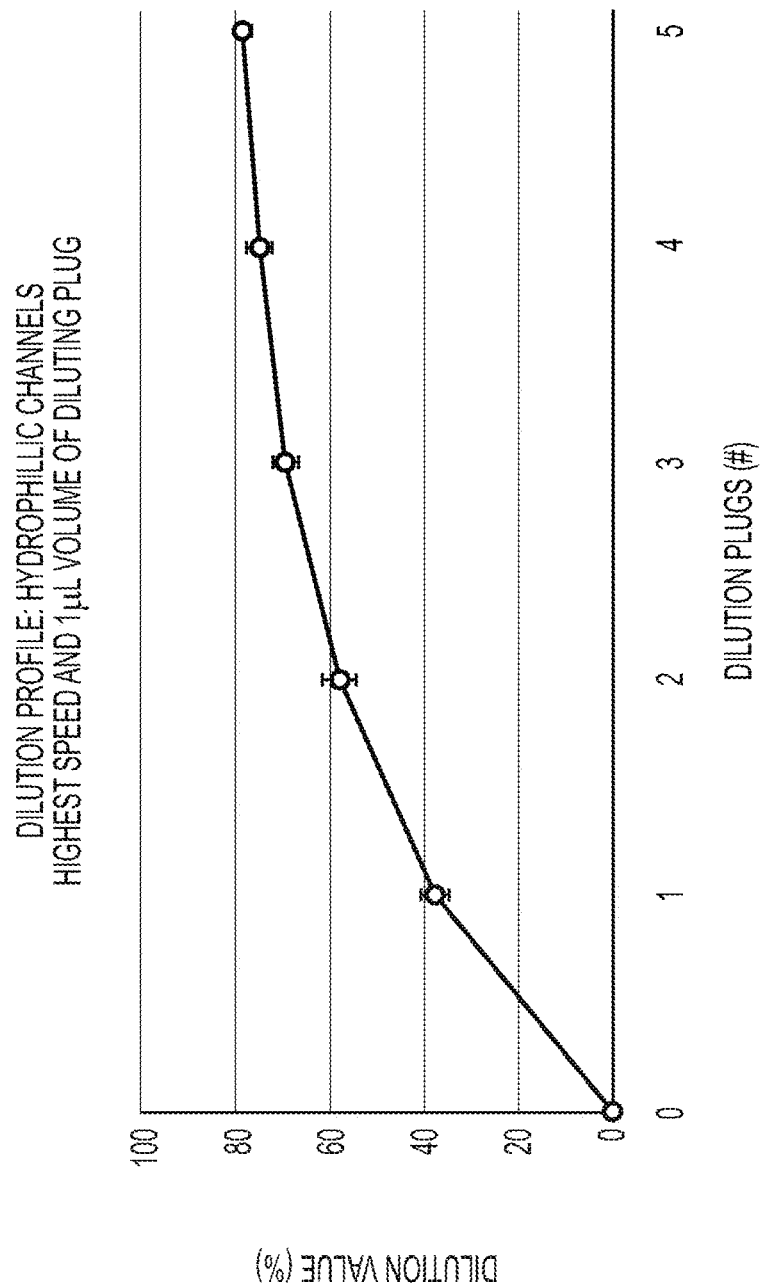

With reference now to FIGS. 7A-7C, shown are graphs illustrating data from dilutions carried out in the hydrophilic design of FIG. 1C using a Matrix™ sixteen (16) channel electronic pipettor from Thermofisher Scientific. The amount of dilution in the microfluidic chambers can be varied by varying either: (a) the volume of the diluting fluid stream, with the results shown in FIG. 7A; (b) the number of diluting plugs, with the results shown in FIGS. 7B and 7C. As can be seen from the graphs, the co-efficient of variation (CV) of the dilution is typically ≤5%.

Figure 8A:
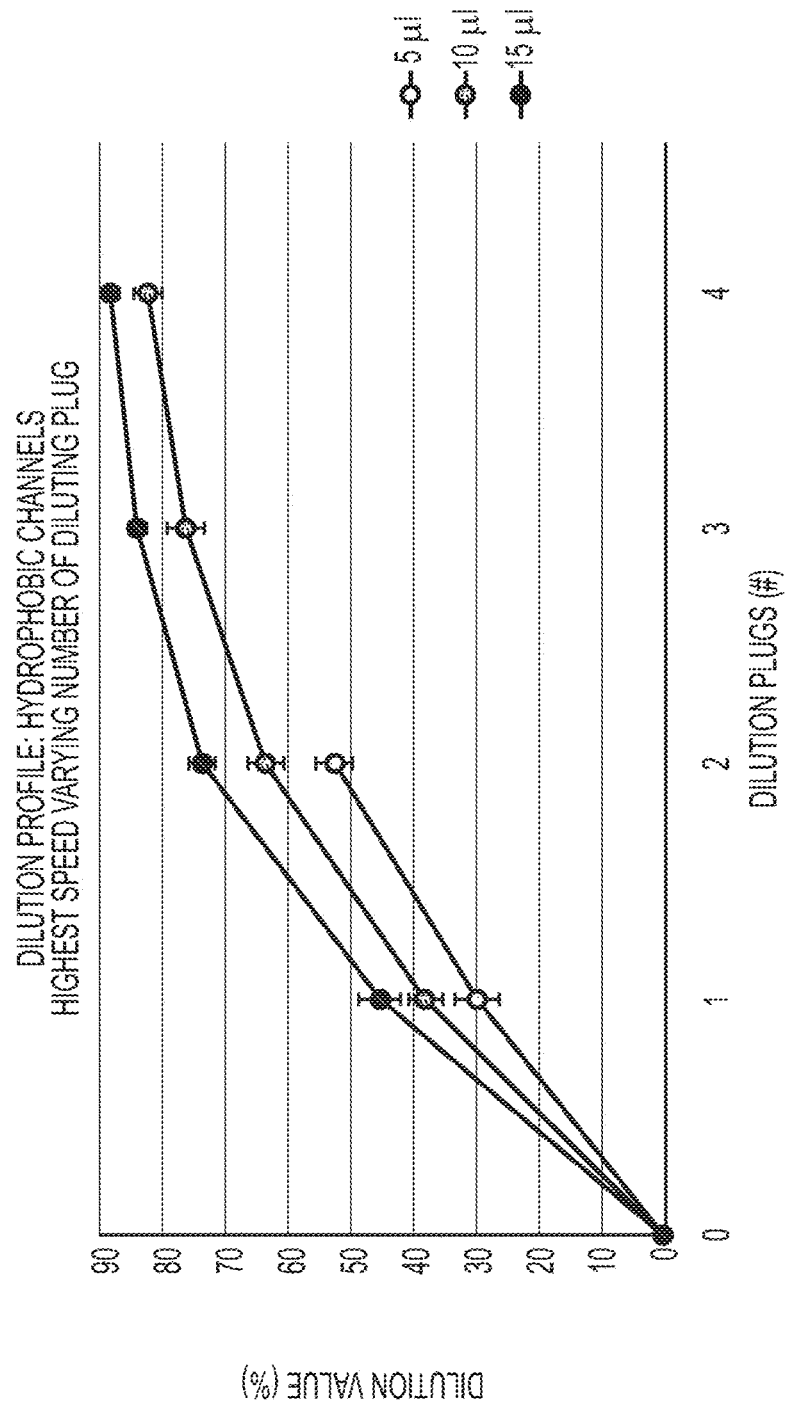
FIGS. 8A-8B are graphs illustrating data from dilutions using a hydrophobic embodiment of the microfluidic serial dilution platform based well-plate using an oil-free immiscible phase driven by manual or electronic pipettors.
Figure 8B:
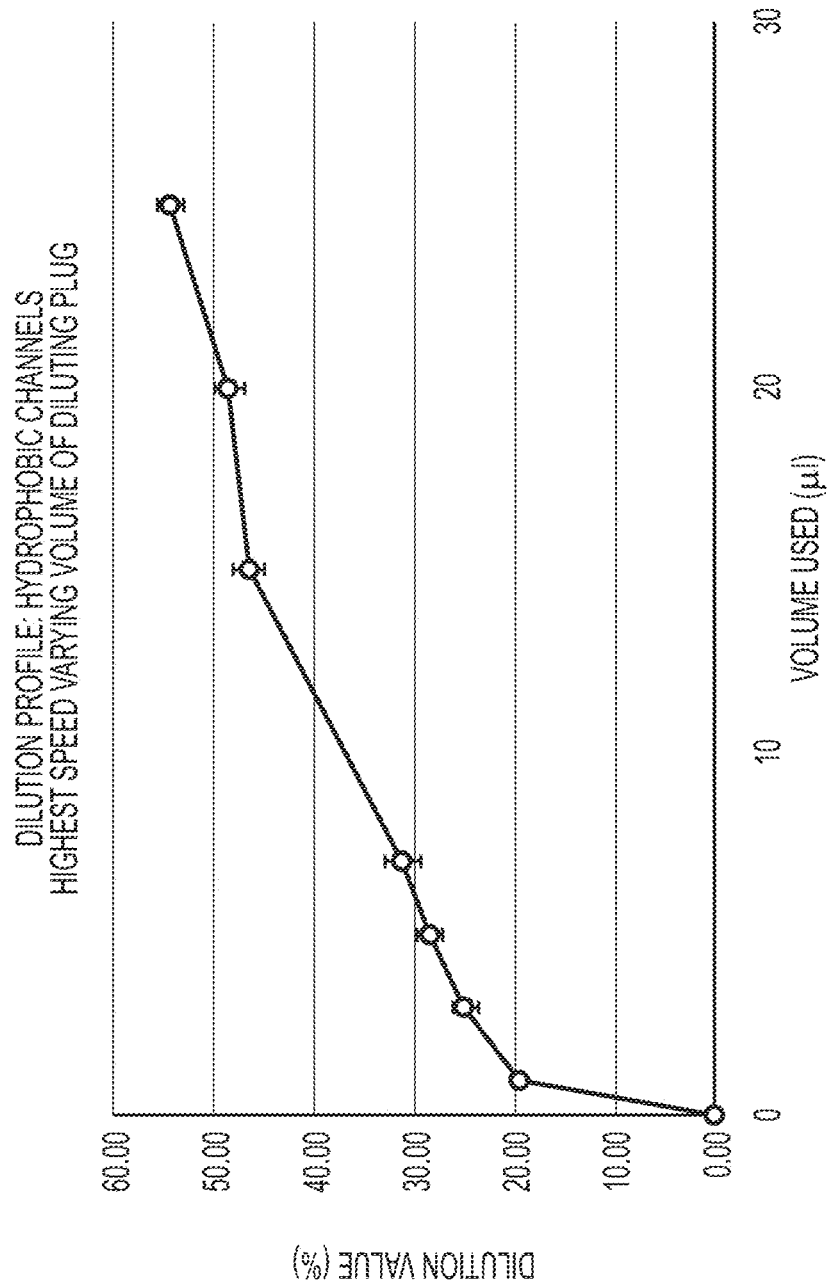

With reference now to FIGS. 8A-8B, shown are graphs illustrating data from dilutions carried out in a hydrophobic design of FIG. 1C using a Matrix™ sixteen (16) channel electronic pipettor from Thermofisher Scientific. The graph in FIG. 8A illustrates the varying amount of dilutions that can be accomplished using varying volumes of diluting plugs and varying numbers of such diluting plugs. The graph in FIG. 8B illustrates the varying amounts of dilutions that can be accomplished using varying volumes of diluting plugs.

Figure 9B:
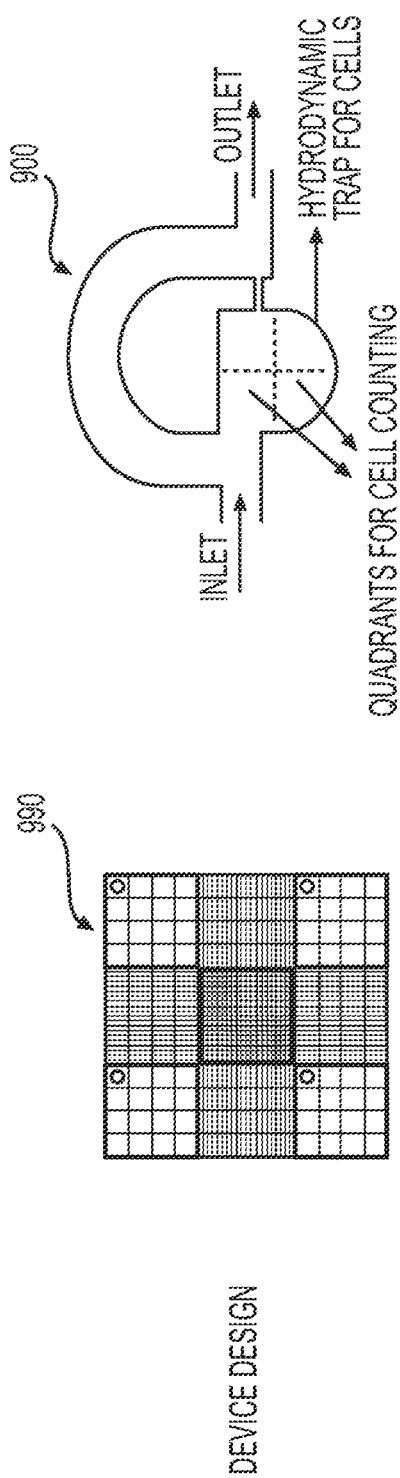
FIG. 9B is a diagram illustrating a hydrophobic embodiment of the microfluidic serial dilution platform based well-plate using an oil-free immiscible phase driven by manual or electronic pipettors used a hemocytometer.

With reference to FIGS. 9A-9C, tables and diagrams are shown illustrating the embodiments of a microfluidic serial dilution platform based well-plate that may also be used as a hemocytometer. The embodiment shown is a hydrophobic design (e.g., see FIGS. 6A-6B). With reference to FIG. 9A, a table is shown illustrating cell counts made with a standard hemocytometer as well as an embodiment of a microfluidic serial dilution platform based well-plate. The table illustrates two cell counting experiments: (1) an experiment performed with a standard hemocytometer diluted with trypan blue, a dye used to determine between live/dead cells, and a microfluidic serial dilution platform based well-plate without dilution by trypan blue and (2) an experiment performed with a standard hemocytometer diluted with trypan blue and a microfluidic serial dilution platform based well-plate with dilution by trypan blue. The cell counting formula used is a common protocol associated when using a hemocytometer, where the cell count is multiplied by both the dilution factor and the conversion factor. With reference to FIG. 9B, a hydrophobic implementation of a microfluidic serial dilution platform based well-plate 900 with traps gridded into quadrants each for cell counting. A depiction of a standard gridded hemocytometer 990 is also shown.

A cell suspension may be loaded using either a manual or electronic pipette into a gridded microfluidic trap. The cells within the traps were counted and used to calculate the total population. In the first experiment, the cell count using a standard hemocytometer with trypan blue took six minutes and twenty-two seconds (6:22) and produced counts of 180, 182, 225, and 83 totaling to 670. Applying the conversion factor, the count became $670e^4$ which is the same as $6.7 \times 10^6$ cells/ml. Including the entire suspension volume, the total count from the standard gridded hemocytometer resulted in $20.1 \times 10^6$ total cells. The count using an implementation of microfluidic serial dilution platform based well-plate 900 with traps gridded into quadrants took only thirty seconds (0:30). Within six traps, the quadrants totaled to 681, 659, 667, 610, 641, and 734, producing an average of 665 cells/0.1 µl, which converts to 6653 cells/µl, equaling $6.65 \times 10^6$ cells/ml. With the same suspension volume, this method calculated to a total of $19.9 \times 10^6$ cells. The results for the second experiment were obtained using the same methods and produced values that were equally close.

A comparison of results obtained from the implementation of a microfluidic serial dilution platform based well-plate and those obtained using a conventional hemocytometer shows reasonably similar cell counts. The microfluidic serial dilution platform based well-plate shows excellent reproducibility and presents further advantages over conventionally used hemocytometers one such being the time required, as illustrated in FIG. 9C.

Experiments with embodiments described herein demonstrate that microfluidic serial dilution platform based well-plate may perform various assays completely on-chip (i.e., on a chip or other suitable substrate containing (how many traps within a given chip. For example, experiments showed Clenbuterol ELISA assays may be performed completely on-chip using an electronic pipette. In an experiment, the varying degrees of dilution of the sample using the buffer and substrate solutions were accomplished using the graphs for dilution presented in FIGS. 7A-7C and FIGS. 8A-8B. Microscopic images of the experiments demonstrated that the samples with most amount of drug had no coloration where samples with the least amount of drug below the threshold value have higher values of coloration as expected. Advantages of using ELISA-based assays with embodiments of the present invention include: (a) reduced time to conduct tests (nearly one-third the time compared to conventional methods; (b) higher sensitivity due to an increased surface to volume ratio; and (c) increased accuracy due to a conserved volume that does not change.

Figure 10A:
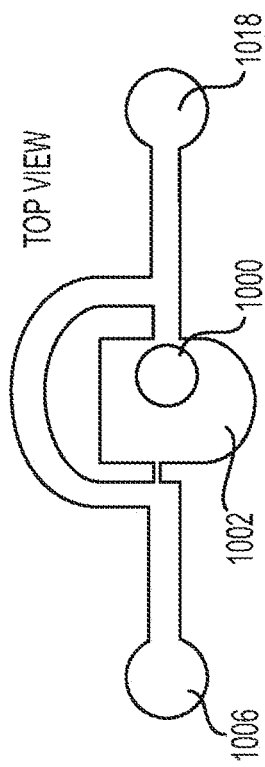
FIGS. 10A and 10B are diagrams illustrating an embodiment of a microfluidic serial dilution platform based well-plate using an oil-free immiscible phase driven by manual or electronic pipettors with a cover on top of the well-plate to maintain humidity and control evaporation from the fluidic trap.
Figure 10B:
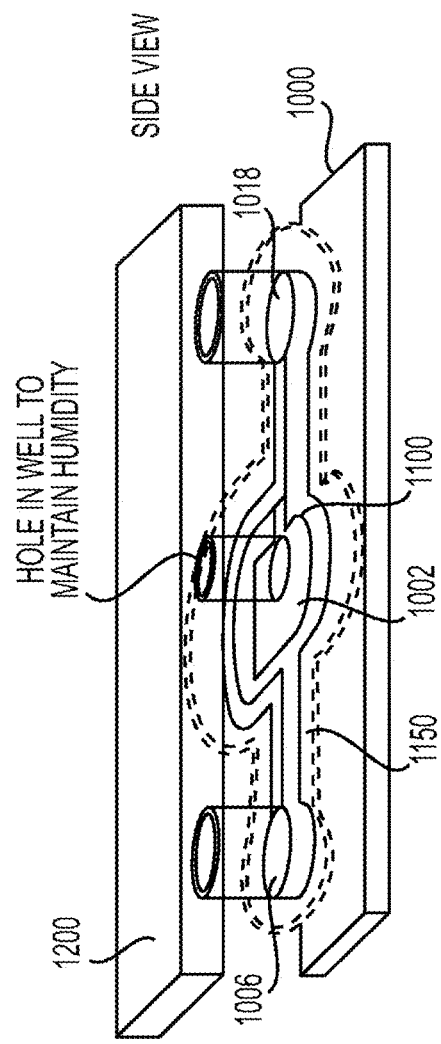
Figure 10C:
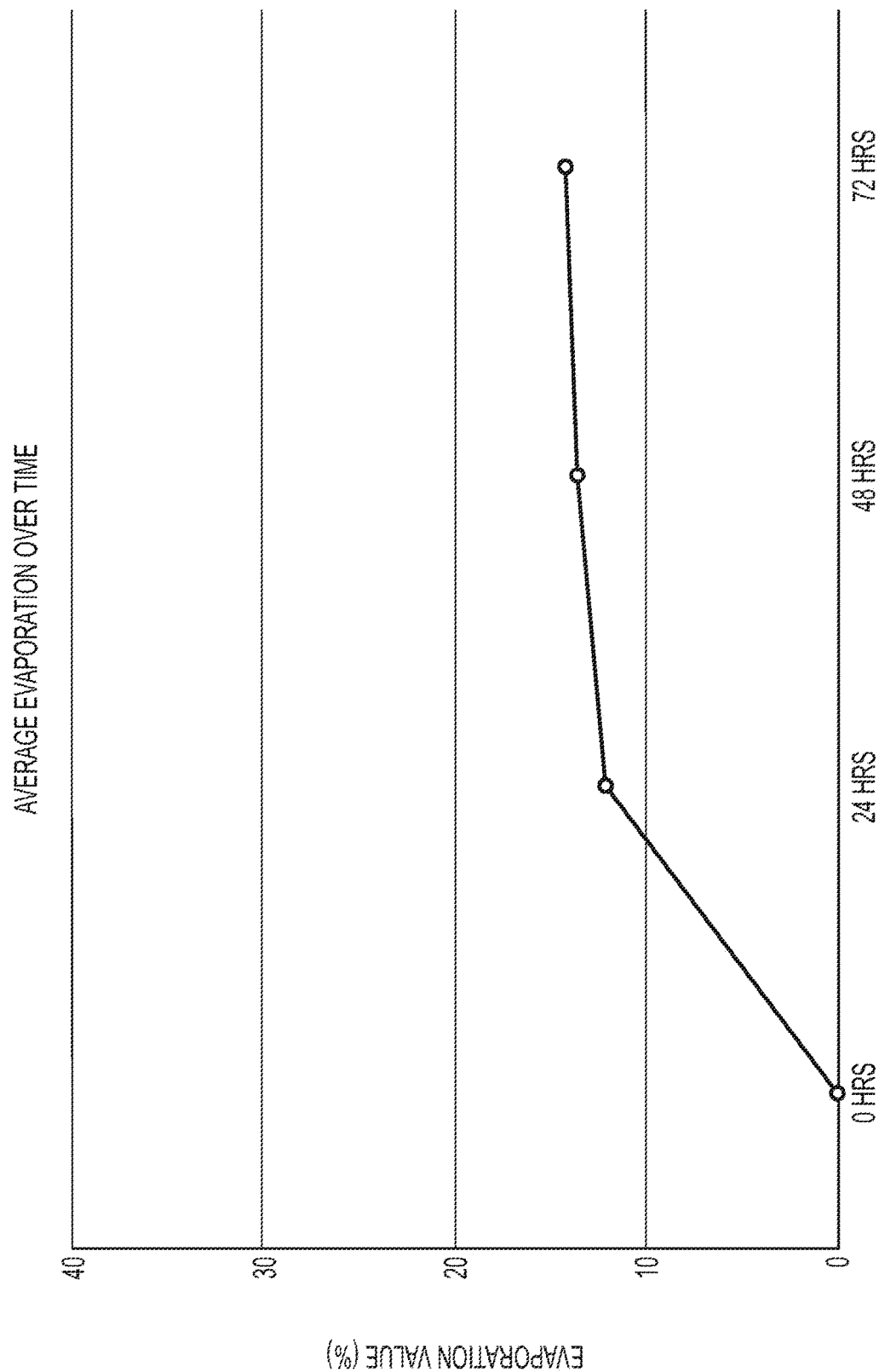
FIG. 10C is a graph illustrating average evaporation rates using the embodiment shown in FIGS. 10A and 10B.

With reference now to FIGS. 10A-C, shown is an embodiment of microfluidic serial dilution platform based well-plate that controls the evaporation of fluid from the fluidic traps. If evaporation of fluid from the traps needs to be controlled as is the case when performing cell based assays the device is configured as shown. With reference to FIG. 10A, shown is a top view of this configuration which includes a hole 1100 drilled into each trap 1002 of the microfluidic network (specifically, hole 1100 is drilled through cover enclosing trap 1002). In this manner, trap 1002 is not fully enclosed by cover. However, this hole 1100 is covered at all times while microfluidic serial dilution platform based well-plate is in use by a material different than the cover. As discussed above, each trap in the microfluidic trap network is covered by cover (e.g., cover 1200) while hole 1100, which extends through cover, is covered by cellophane or similar material that is airtight. The covered hole maintains humidity in the trap to prevent evaporation of fluid in the trap. Note: the fluidic trap 1002 shown in FIG. 10A is not square; rather trap 1002 has a rounded or semi-circular bottom. With reference to FIG. 10B, shown is a perspective view of this embodiment of microfluidic serial dilution platform based well-plate 1000. A reservoir 1150, situated on well-plate 1000 and filled with fluid, such as water, at a fixed pressure, surrounds the microfluidic network. After the trap 1002 is filled with fluid, e.g., a cell solution, a cover 1200 is placed over the microfluidic serial dilution platform based well-plate covering the inlet 1006, outlet 1018, the hole 1100 and the reservoir 1150 (note cover 1200 is shown in suspended above microfluidic serial dilution platform based well-plate; in use, it would be directly in contact and actually cover microfluidic network). With reference to FIG. 10C, shown is a graph depicting the amount of evaporation in the well after various time points using the embodiment illustrated in FIGS. 10A-B. As can be seen the maximum evaporation is less than fifteen percent (15%) after a time period of seventy-two (72) hrs.

Figure 11:
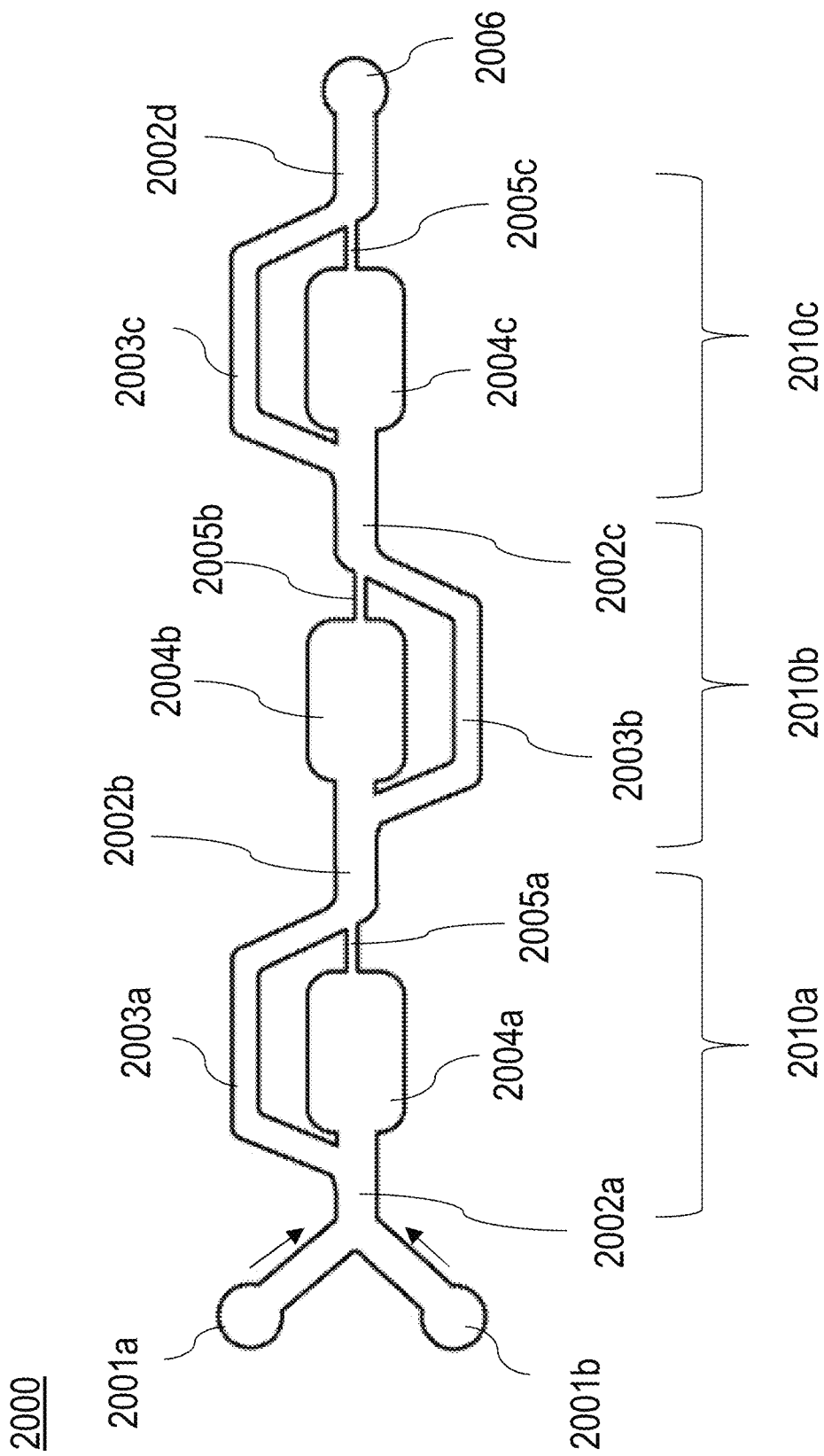
FIG. 11 shows a diagram of an embodiment of a microfluidic serial dilution platform based well-plate of the disclosed invention, which has two inlets and can be driven by manual or electronic pipettors.

With reference to FIG. 11, shown is a diagram of an embodiment of a microfluidic serial dilution platform based well-plate 2000 of the disclosed invention, which can be driven by electronic pipettors. The well-plate 2000 may be formed of wells 2010a, 2010b, 2010c that are connected in series. Well 2010a includes a bypass channel 2003a, a fluidic trap 2004a, and a capillary constriction channel 2005a. The well-plate 2000 includes a plurality of inlets 2001a, 2001b. The well 2010a is connected to the inlets 2001a, 2001b through a main channel 2002a, and may be connected to another well 2010b downstream or outlet 2006 through a main channel 2002b. Capillary constriction channel 2005a is connected to the fluidic trap 2004a in series. In the embodiment shown in FIG. 11, the capillary constriction channel 2005a is connected to an outlet side of the fluidic trap 2005a, but in another embodiment, the capillary constriction channel 2005a may be connected to an inlet side (toward the inlets 2001a, 2001b) of the fluidic trap 2005a. Main channels 2002a, 2002b, 2002c, 2002d with a plurality of portions connect the inlets 2001a, 2001b to the plurality of fluidic traps 2004a, 2004b, 2004c, associated hydrophilic capillary constriction channels 2005a, 2005b, 2005c and associated bypass channels 2003a, 2003b, 2003c, and the outlet 2006.

The fluidic traps 2004a, 2004b, 2004c have larger widths than the associated bypass channels 2003a, 2003b, 2003c to trap fluid in said each fluidic trap while the fluid is removed from the associated bypass channel. The constriction channels 2005a, 2005b, 2005c have smaller widths than the associated fluidic traps 2004a, 2004b, 2004c and the associated bypass channels 2003a, 2003b, 2003c. The constriction channels 2005a, 2005b, 2005c are hydrophilic or hydrophobic channels. The bypass channels 2003a, 2003b, 2003c and the associated fluidic trap 2004a, 2004b, 2004c are connected in parallel. The constriction channels 2005a, 2005b, 2005c and the associated fluidic trap 2004a, 2004b, 2004c are connected in series. When the well 2010a is connected to another well 2010b at downstream, the outlet side main channel 2002b of the well 2010a may become an inlet side main channel of the well 2010b. For illustration purpose, FIG. 11 shows three wells 2010a, 2010b, 2010c, but the number of wells are not limited. As shown in FIG. 1D, a plurality of wells may be connected in series to form a network of the wells.

In the embodiment shown in FIG. 11, the well-plate 2000 has two inlets 2001a, 2001b that allow simultaneous flow of two fluid streams into the well-plate 2000. For description purpose, FIG. 11 shows two inlets 2001a, 2001b. However, the well-plate 2000 of the disclosed invention may have more than two inlets based on applications to allow multiple fluid streams to enter the well-plate 2000 simultaneously. This structure of the embodiment shown in FIG. 11 allows the two or more fluids that enter into the well-plate 2000 to mix more efficiently than compared to when fluids mixing under similar hydraulic diameter channels. This can be useful to form nanoparticles that encapsulate gene delivery vehicles such as sRNA, mRNA under much lower shear stress/pressure-drop/shear rate conditions compared to other methods which might cause the mRNA to degrade at harsh mixing conditions.

In the embodiment shown in FIG. 11, for example, one stream of fluid can carry alcohol along with dissolved polymer or other encapsulating agent, and another stream of fluid can be aqueous fluid containing load or drug. When mixing of the two streams of fluids occur, spontaneous self-assembly follows resulting into a formulation of nanoparticles. The fluid streams may be introduced simultaneously or introduced one after another.

Figure 17A:
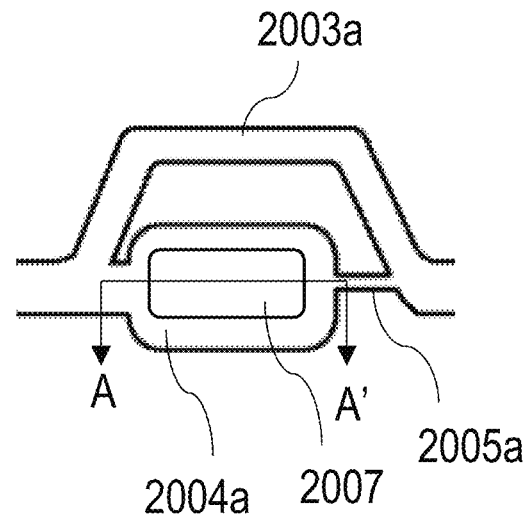
FIGS. 17A-17B show a top view of the fluidic trap and a cross-sectional view of section A-A' shown in FIG. 17A, respectively.
Figure 17B:
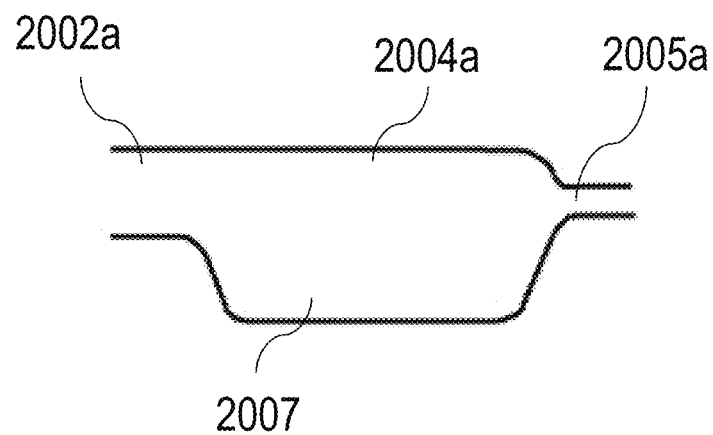

In the embodiments, the lengths of the hydrophilic or hydrophobic constriction channels can be made shorter or longer, and the widths of the hydrophilic or hydrophobic constriction channels can be different. In other words, the lengths and/or widths of some or all of the constriction channels 2005a, 2005b, 2005c may be different from each other. The fluidic trap 2004a may have a recess 2007 at a bottom of the fluidic trap 2004a. With reference to FIGS. 17A-17B, shown are a top view of the fluidic trap and a cross-sectional view of section A-A' of FIG. 17A, respectively, showing an exemplary structure of the recess 2007. The recesses 2007 may formed at bottoms of other fluidic traps 2004a, 2004b, 2004c.

Figure 12:
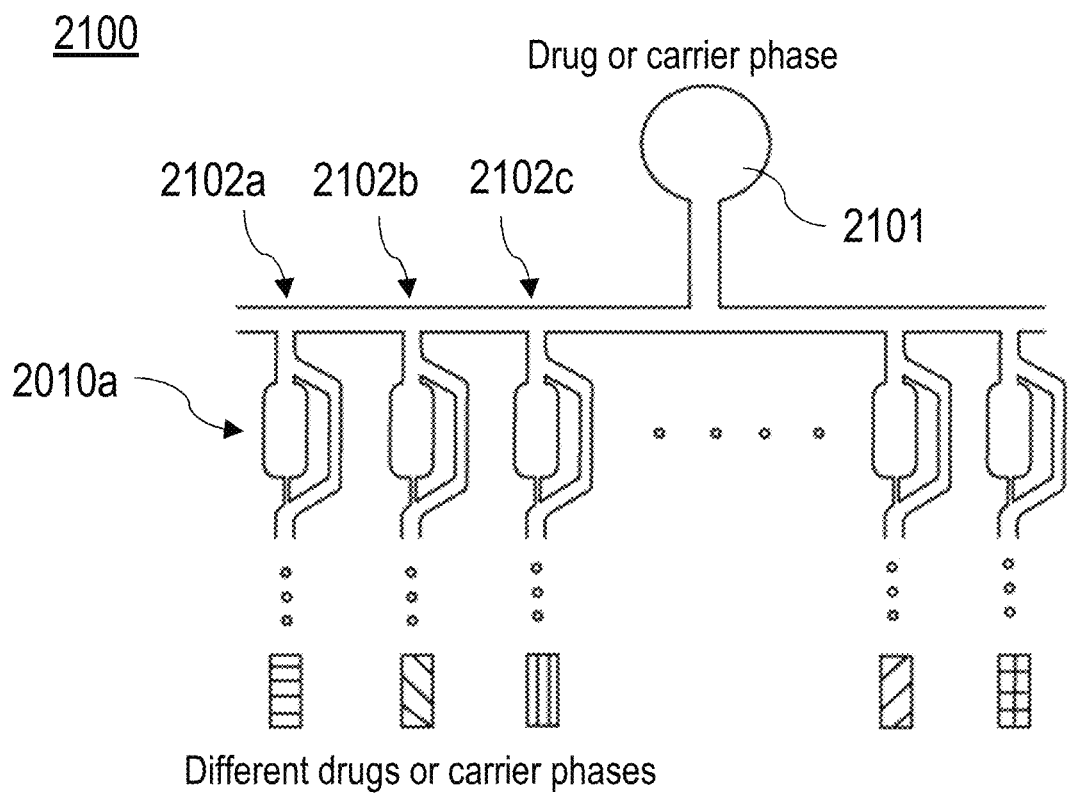
FIG. 12 shows a diagram of an embodiment with multiplexed well-plate for multiplexed screening of delivery vehicle for gene therapy using mixing with static filled traps (nanoliters-microliters).

With reference to FIG. 12, shown is a diagram of an embodiment with multiplexed well-plate for multiplexed screening of delivery vehicle for gene therapy using mixing with static filled traps (nanoliters-microliters). The multiplexed well-plate 2100 includes a plurality of microfluidic serial dilution platform based well-plates 2102a, 2102b, 2102c connected in parallel. Each serial platform 2102a, 2102b or 2102c may include one or more wells 2010a connected in series. Each well 2010a includes fluidic trap 2004a and associated bypass channel 2003a and associated capillary constriction channel 2005a. The multiplexed array of well-plates 2102a, 2102b, 2102c are connected to an central input channel 2101 that may include one or more inlets to introduce fluid streams sequentially or simultaneously into the multiplexed well-plate 2100. Wells 2010a in well-plates 2102a, 2102b, 2102c may have different configurations. For example, capillary constrictions channels 2005a may have different lengths and/or widths, and fluidic traps 2004a may have different sizes.

In the embodiment shown in FIG. 12, in order to achieve high throughput screening of nanoparticle delivery vehicles using low sample volumes, the trap may be first filled with the drug/therapeutic to be delivered followed by flowing the non-aqueous stream containing the enclosing polymer. The traps can be "multiplexed" using a central splitting network to conduct high throughput studies with samples trapped in wells ranging in volume from nano-liters to a few microliters. This may be particularly important in designing delivery vehicles for gene therapy (e.g. mRNA).

With reference to FIGS. 13A-13D, shown are embodiments on in-vitro screening of cells against drugs. After cells are introduced into the fluidic traps, the cells are loaded in the fluidic traps, when the associated capillary constriction channels are filled with air (FIG. 13A), and are allowed to attach and culture in the fluidic traps (FIG. 13B). The constriction channels work as valves when they are filled with air due to the large surface tension at the micro scale. The capillary constriction channels may be hydrophobic. Dissolvable beads are loaded into the traps after cells are cultured (FIG. 13C). Dissolvable beads containing the drug can be loaded by sieving when the valve is closed (while the constriction channels are filled with fluid), allowing one bead per chamber (fluidic trap), as shown in FIG. 13D. The dissolvable beads can be prepared using the method described referring to FIG. 12. The traps are isolated after passing an immiscible phase. Each trap then is independent of the others in series since beads contain different compounds. The polymer concentration of the beads can be tailored to have a pharmacokinetic (PK) like profile allowing high throughput screening of drugs such as protein degraders whose pharmacological effects differ on the time course of the reaction.

Figure 14:
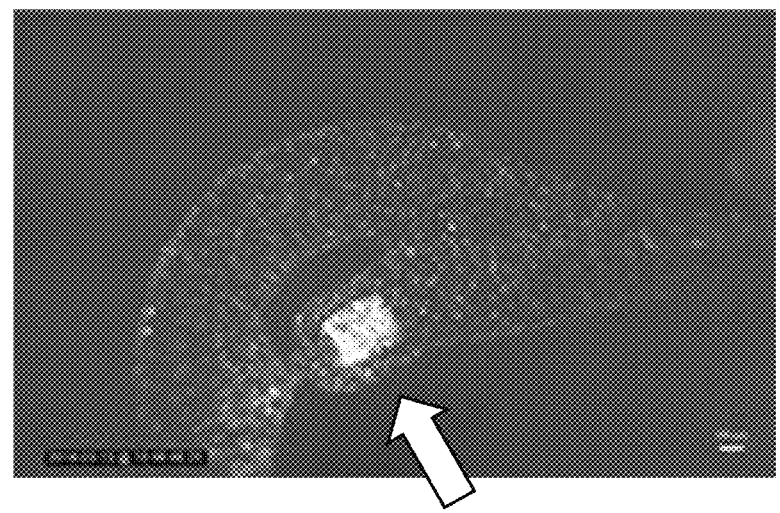
FIG. 14 shows trapped culture and maintain suspension cells with flow after fluidic constriction is filled with fluid.

With reference to FIG. 14, shown is trapped culture of suspension cells with flow after fluidic constriction is filled with fluid. Arrow refers to suspension cells in a recessed part of the trap. The recessed part allows fluid to flow over the cells filled in the recessed part. Allowing constant perfusion of suspension cells for kinetic drug screening.

In these configurations, the traps after they are formed eventually close e.g. for cell culture such that when fluid is re-introduced it flows over the adherent cells or suspension cells that are first introduced and is trapped where the trap has recess 2007 in the middle allowing the suspension cells to settle after any fluid introduced into it flows "over it" as it is in the recess (as shown in FIG. 14). In addition 3D culture of cells is also possible with commercially available supports like Matrigel. In this case the support along with the cells in flowed in at liquid state by maintain the temperature of the chip below 4 degrees centigrade, Traps are then formed and temperature is brought to cell culture temperature allowing the substrate to form a support for the cells only in the wells and also allowing media and other fluids to flow around it. Further through controlling flowrate of fluid flowing through the traps it is possible to achieve controlled concentration profiles by having two inlets, for example, one with media and one with drug. The method is particularly suited for screening degraders (Proteolysis Targeting Chimeras), for example, when there is a pharmacokinetics and pharmacodynamics (PK-PD) disconnect and washout is required to determine the catalytic activity of the drug degrading the proteome of interest which could be labelled through clustered regularly interspaced short palindromic repeats (CRISPR) based methods in order to identify rate of degradation.

With reference to FIG. 15, shown is a flowchart for a method 2200 of operating a microfluidic serial dilution platform based well-plate of the disclosed invention. A first fluid and a second fluid are simultaneously introduced into a first inlet and a second inlet, respectively, block 2201. The first and second fluids are caused to enter into a bypass channel associated with a fluidic trap, block 2202. The bypass channel and the associated fluidic trap are connected in parallel. The first and second fluids are caused to enter into the fluidic trap until the fluidic trap is filled with the first and second fluids, block 2203. The first and second fluids are mixed in the fluidic trap, block 2204.

In one embodiment, the first fluid may include alcohol with dissolved polymer or encapsulating agent and the second fluid may be an aqueous fluid containing load or drug. The polymer or encapsulating agent from the first fluid and the load or drug from the second fluid may be self-assembled in the fluidic trap forming nanoparticles with drug or load encapsulated. In another embodiment, the first fluid may include media and the second fluid may include drug. The method may further includes controlling flowrates of the first fluid and the second fluid while introducing the first and second fluids into the first and second inlets, respectively, to control a concentration of the drug in the media.

Figure 16:
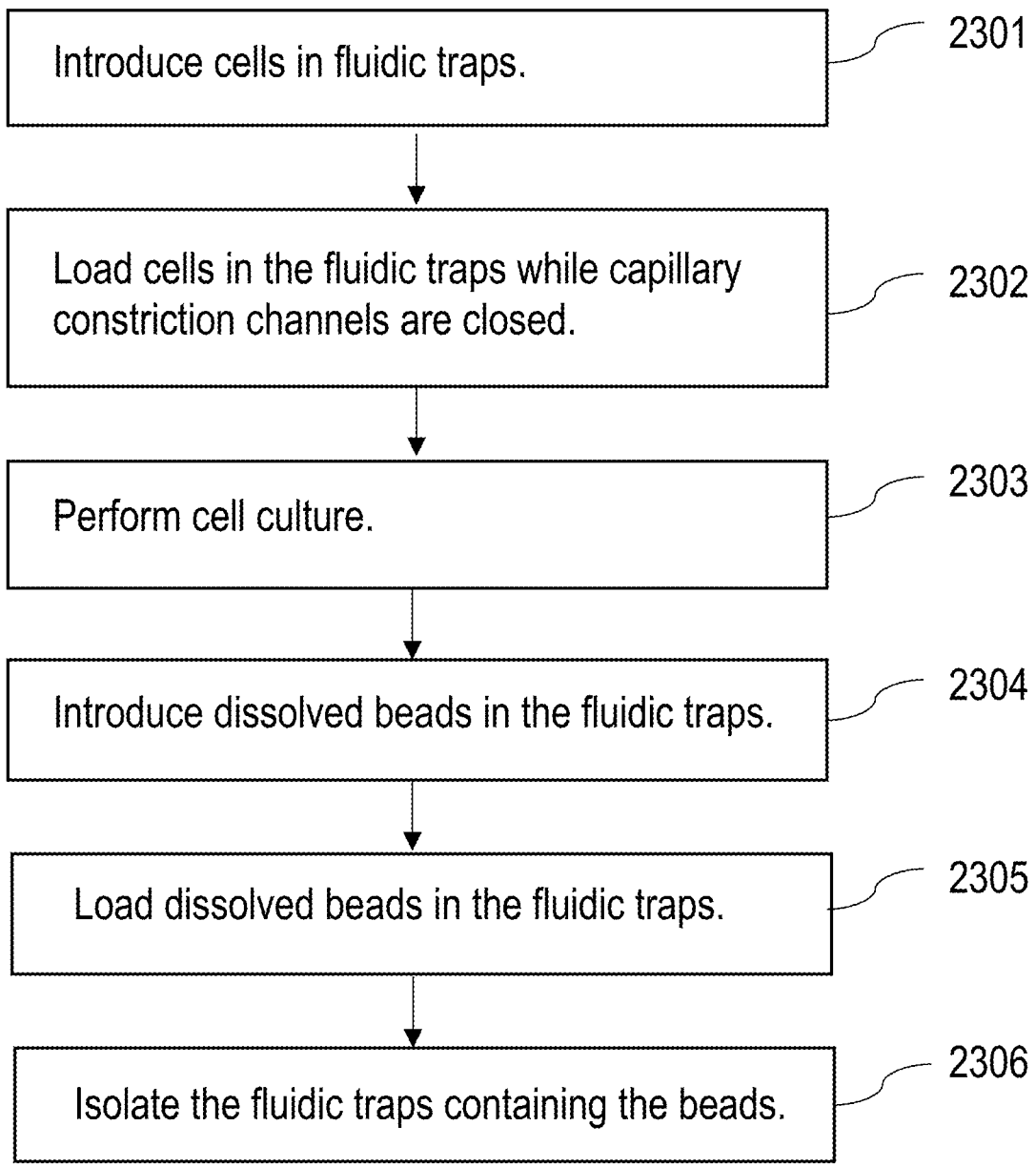
FIG. 16 shows a flowchart for a method of operating a microfluidic serial dilution platform based well-plate of the disclosed invention for in-vitro screening of cells against drugs.

With reference to FIG. 16, shown is a flowchart for a method 2300 of operating a microfluidic serial dilution platform based well-plate of the disclosed invention for in-vitro screening of cells against drugs. Cells are introduced in fluidic traps connected in series, block 2301. The cells are loaded in the fluidic traps while capillary constriction channels associated with the fluid traps are closed, block 2302. Cell culture is performed for the cells loaded in the fluidic traps, block 2303. Dissolved beads containing drugs are introduced into the fluidic traps, block 2304. The dissolved beads are loaded in the fluidic traps, block 2305. The fluidic traps containing the beads are isolated, block 2306. The fluidic traps may be constructed to have recesses formed at bottoms of the fluidic traps and the cells are loaded in the recesses of the fluidic traps. The capillary constriction channels are closed by filling the capillary constriction channel with air. The fluidic traps may be isolated by filling the bypass channels with air.

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated.

What is claimed is:

1. A microfluidic device, comprising:
a plurality of fluidic traps;
a plurality of capillary constriction channels, wherein each of the plurality of capillary constriction channels is associated with one of the plurality of fluidic traps;
a plurality of bypass channels, wherein each of the plurality of bypass channels is associated with one of the plurality of fluidic traps, and wherein each fluidic trap and the associated bypass channel are connected in parallel and each fluidic trap and the associated capillary constriction channel are connected in series;
a plurality of inlets connected to the fluidic traps and bypass channels, wherein the inlets are configured to simultaneously supply multiple fluid streams towards the fluidic traps and the associated bypass channels;
an outlet; and
a main channel with a plurality of portions that connects the inlet to the plurality of fluidic traps, associated capillary constriction channels and associated bypass channels, and the outlet.

2. The microfluidic device of claim 1 wherein the constriction channels have different lengths and/or different widths.

3. The microfluidic device of claim 1 wherein sets of the fluidic traps and associated bypass channels are arranged in a serial circuit with each other.

4. The microfluidic device of claim 1 wherein the fluidic traps are constructed to have recesses formed at bottoms of the fluidic traps.

5. The microfluidic device of claim 1 wherein the capillary constriction channels are connected to downstream sides of the associated fluidic traps.

6. The microfluidic device of claim 1 wherein the capillary constriction channels are hydrophobic constriction channels.

7. The microfluidic device of claim 1 wherein the capillary constriction channels are connected to upstream sides of the associated fluidic traps.

8. The microfluidic device of claim 1 wherein the capillary constriction channels are hydrophilic constriction channels.

9. The microfluidic device of claim 1 wherein the inlets include interfaces for a pipettor, pipette or other fluid driving mechanism.

10. A microfluidic device, comprising:
a plurality of fluidic traps connected in parallel;
a plurality of capillary constriction channels, wherein each of the plurality of capillary constriction channels is associated with one of the plurality of fluidic traps;
a plurality of bypass channels, wherein each of the plurality of bypass channels is associated with one of the plurality of fluidic traps, and wherein each fluidic trap and the associated bypass channel are connected in parallel and each fluidic trap and the associated capillary constriction channel are connected in series;
one or more inlets connected to the fluidic traps; and
a plurality of outlets wherein each of the outlets is associated with one of the plurality of fluidic traps.

11. The microfluidic device of claim 10 wherein the constriction channels have different lengths and/or different widths.

12. The microfluidic device of claim 10 wherein the capillary constriction channels are connected to downstream sides of the associated fluidic traps.

13. The microfluidic device of claim 10 wherein the capillary constriction channels are hydrophobic constriction channels.

14. The microfluidic device of claim 10 wherein the capillary constriction channels are connected to upstream sides of the associated fluidic traps.

15. The microfluidic plate of claim 10 wherein the capillary constriction channels are hydrophilic constriction channels.

16. A method of operating a microfluidic serial dilution platform based well-plate, comprising:
introducing simultaneously a first fluid into a first inlet and a second fluid into a second inlet;
causing the first and second fluids to enter into a bypass channel associated with a fluidic trap, wherein the bypass channel and the associated fluidic trap are connected in parallel;
causing the first and second fluids to enter into the fluidic trap until the fluidic trap is filled with the first and second fluids; and
causing the first and second fluids to be mixed in the fluidic trap.

17. The method of claim 16 wherein the first fluid includes alcohol with dissolved polymer or encapsulating agent and the second fluid is an aqueous fluid containing load or drug.

18. The method of claim 17 wherein the polymer or encapsulating agent from the first fluid and the load or drug from the second fluid are self-assembled in the fluidic trap forming nanoparticles with drug or load encapsulated.

19. The method of claim 16 wherein the first fluid includes media and the second fluid includes drug.

20. The method of claim 19 further comprising controlling flowrates of the first fluid and the second fluid while introducing the first and second fluids into the first and second inlets, respectively, to control a concentration of the drug in the media.

21. A method of operating a microfluidic serial dilution platform based well-plate, comprising:
introducing cells in fluidic traps connected in series;
loading cells in the fluidic traps while capillary constriction channels associated with the fluid traps are closed;
performing cell culture for the cells loaded in the fluidic traps;
introducing dissolved beads containing drugs into the fluidic traps;
loading the dissolved beads in the fluidic traps; and
isolating the fluidic traps.

22. The method of claim 21 wherein the fluidic traps are constructed to have recesses formed at bottoms of the fluidic traps and the cells are loaded in the recesses of the fluidic traps.

23. The method of claim 21 wherein the capillary constriction channels are closed by filling the capillary constriction channel with air.

24. The microfluidic device of claim 1 wherein the microfluidic device is a well plate.

25. The microfluidic device of claim 1 wherein the microfluidic device is made of cyclin olefin copolymer (COC).

* * * * *

UNITED STATES PATENT AND TRADEMARK OFFICE
CERTIFICATE OF CORRECTION

PATENT NO. : 12,290,811 B2  
APPLICATION NO. : 17/134737  
DATED : May 6, 2025  
INVENTOR(S) : Deepak Solomon Page 1 of 1

It is certified that error appears in the above-identified patent and that said Letters Patent is hereby corrected as shown below:

In the Claims

Column 15, Claim 15, Line 18:
"microfluidic plate"

Should read:
--microfluidic device--

Signed and Sealed this  
First Day of July, 2025

Coke Morgan Stewart  
*Acting Director of the United States Patent and Trademark Office*